United States Patent
Davis et al.

(10) Patent No.: US 11,456,057 B2
(45) Date of Patent: Sep. 27, 2022

(54) BIOLOGICAL SEQUENCE DISTANCE EXPLORER SYSTEM PROVIDING USER VISUALIZATION OF GENOMIC DISTANCE BETWEEN A SET OF GENOMES IN A DYNAMIC ZOOMABLE FASHION

(71) Applicant: International Business Machines Corporation, Armonk, NY (US)

(72) Inventors: Matthew Davis, San Jose, CA (US); James Kaufman, San Jose, CA (US); Mark Kunitomi, San Francisco, CA (US)

(73) Assignee: International Business Machines Corporation, Armonk, NY (US)

(*) Notice: Subject to any disclaimer, the term of this patent is extended or adjusted under 35 U.S.C. 154(b) by 779 days.

(21) Appl. No.: 15/940,457

(22) Filed: Mar. 29, 2018

(65) Prior Publication Data
US 2019/0303534 A1   Oct. 3, 2019

(51) Int. Cl.
*G16B 30/00* (2019.01)
*G16B 40/00* (2019.01)
*G16B 45/00* (2019.01)
*G16B 50/00* (2019.01)

(52) U.S. Cl.
CPC ............. *G16B 30/00* (2019.02); *G16B 40/00* (2019.02); *G16B 45/00* (2019.02); *G16B 50/00* (2019.02)

(58) Field of Classification Search
None
See application file for complete search history.

(56) References Cited

U.S. PATENT DOCUMENTS

| | | |
|---|---|---|
| 7,894,984 B2 | 2/2011 | Rasmussen et al. |
| 2005/0014195 A1 | 1/2005 | Vauterin et al. |
| 2013/0226466 A1 | 8/2013 | Kim |
| 2016/0098519 A1 | 4/2016 | Zwir |
| 2016/0246871 A1 | 8/2016 | Singh et al. |

FOREIGN PATENT DOCUMENTS

| | | |
|---|---|---|
| CN | 105512512 A | 4/2016 |
| CN | 106446603 A | 2/2017 |

OTHER PUBLICATIONS

L'Yi, Sehi, et al. "XCluSim: a visual analytics tool for interactively comparing multiple clustering results of bioinformatics data." BMC bioinformatics 16.S11 (2015): S5. (Year: 2015).*
Wei, Dan, et al. "A novel hierarchical clustering algorithm for gene sequences." BMC bioinformatics 13.1 (2012): 174. (Year: 2012).*
Eisen in Cluster and TreeView Manual; software manual copyright Stanford University 1998-1999; 20 pages.*
Babicki et al. in Nucleic Acids Research (2016) vol. 44; web service issue; pp. W147-W153.*
Yardimci, GG, et al., "Software tools for visualizing Hi-C data" Genome Biology, Feb. 3, 2017, pp. 18:26. Retrieved at: https://doi.org/10.1186/s13059-017-1161-y, Washington, United States.
Pavlopoulos, G.A. et al., "A reference guide for tree analysis and visualization", BioData Mining, 2010, pp. 1-16, Retrieved at: https://biodatamining.biomedcentral.com/articles/10.1186/1756-0381-3-1, BioMed Central, United States.
Ondov, B.D., et al., "Mash: fast genome and metagenome distance estimation using MinHash", Genome Biology, 17:132, pp. 1-14, 2016, Retrieved at: https://genomebiology.biomedcentral.com/articles/10.1186/s13059-016-0997-x, BioMed Central, United States.
Meier-Kolthoff, J.P. et al., "Genome sequence-based species delimitation with confidence intervals and improved distance functions",. BMC Bioinformatics, pp. 1-14, 2013, Retrieved at: http://www.biomedcentral.com/1471-2105/14/60, BioMed Central, United States.
Mullner, D., "Modern hierarchical, agglomerative clustering algorithms", Retrieved at https://arxiv.org/pdf/1109.2378.pdf, Sep. 12, 2011, pp. 1-29, United States.
List of IBM Patents or Patent Applications Treated as Related; Davis, M. et al., U.S. Appl. No. 17/817,631, filed Aug. 4, 2022.

* cited by examiner

*Primary Examiner* — Lori A. Clow
(74) *Attorney, Agent, or Firm* — Sherman IP LLP; Kenneth L. Sherman; Hemavathy Perumal

(57) ABSTRACT

One embodiment provides for a method including determining, by at least one processor, sequence-sequence distances for a biological sequence collection. The at least one processor generates a matrix $M_{ij}$ of the sequence-sequence distances, where i and j are positive integers. The at least one processor further generates clusters for the matrix $M_{ij}$ by performing hierarchical clustering. A self-consistent taxonomy is created from the clusters. A visual heat map display of the matrix $M_{ij}$ is selectively controlled using metadata, zoom input and opacity input.

20 Claims, 20 Drawing Sheets

(11 of 20 Drawing Sheet(s) Filed in Color)

1800

Sequence Input

1810

Name or id

Lb237a

1820

Group

Lactobacillus Primer Set

Sequence

*Sequence Example*

1830 upload

BIOLOGICAL SEQUENCE DISTANCE EXPLORER SYSTEM PROVIDING USER VISUALIZATION OF GENOMIC DISTANCE BETWEEN A SET OF GENOMES IN A DYNAMIC ZOOMABLE FASHION

BACKGROUND

A wide variety of industrial and public health applications require comparing genomes from a set of organisms with each other and with a large database of reference organisms. Medical and Food Safety industries depend on technologies such as PCR (polymerase chain reaction) to classify organisms based on primers (sequences) designed to hit a particular target strain and no other taxa. Identification of new primer sequences, classifying organisms, tracing outbreaks, and identifying pathogenic organisms in a patient or food sample are turning to Whole Genome Sequencing and whole genome or target distance metrics using a growing library of reference genomes. Today there are over 360,000 complete bacterial genomes publicly available.

SUMMARY

Embodiments relate to selectively controlling visual content of biological sequence-sequence distances for a complete biological collection. One embodiment provides for a method including determining, by at least one processor, sequence-sequence distances for a biological sequence collection. The at least one processor generates a matrix $M_{ij}$ of the sequence-sequence distances, where i and j are positive integers. The at least one processor further generates clusters for the matrix by performing hierarchical clustering. A self-consistent taxonomy is created from the clusters. A visual heat map display of the matrix $M_{ij}$ is selectively controlled using metadata, zoom input and opacity input.

These and other features, aspects and advantages of the present invention will become understood with reference to the following description, appended claims and accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18 illustrates an example graphical user interface (GUI) for inputting a sequence, according to one embodiment;

DETAILED DESCRIPTION

Figure 1:
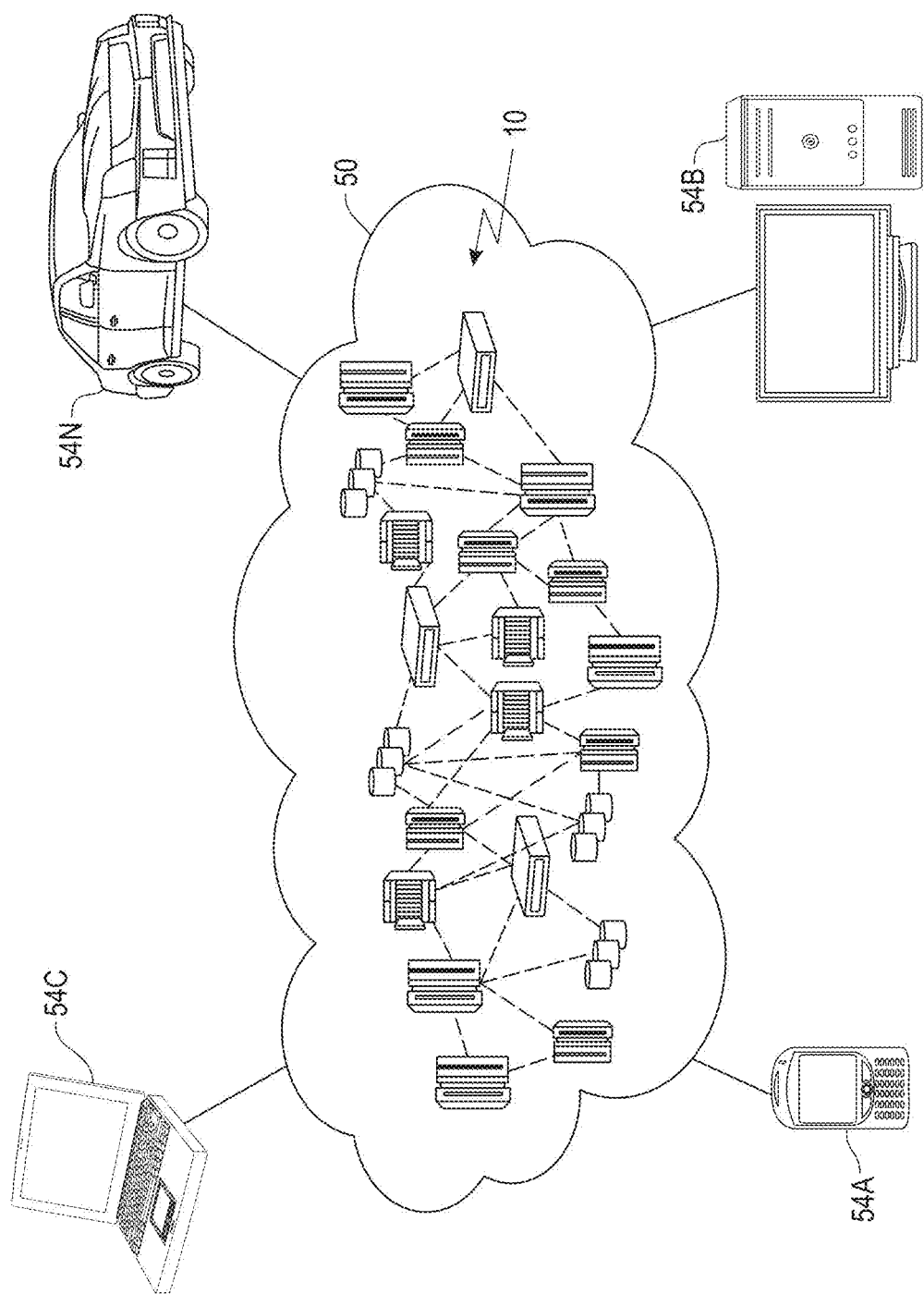
FIG. 1 depicts a cloud computing environment, according to an embodiment.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is understood in advance that although this disclosure includes a detailed description of cloud computing, implementation of the teachings recited herein are not limited to a cloud computing environment. Rather, embodiments of the present invention are capable of being implemented in conjunction with any other type of computing environment now known or later developed.

Embodiments relate to selectively controlling visual content of biological sequence-sequence distances for a complete biological collection. One embodiment provides for a method including determining, by at least one processor sequence-sequence distances for a biological sequence collection. The at least one processor generates a matrix $M_{ij}$ of the sequence-sequence distances, where i and j are positive integers. The at least one processor further generates clusters for the matrix $M_{ij}$ by performing hierarchical clustering. A self-consistent taxonomy is created from the clusters. A visual heat map display of the matrix $M_{ij}$ is selectively controlled using metadata, zoom input and opacity input.

Cloud computing is a model of service delivery for enabling convenient, on-demand network access to a shared pool of configurable computing resources (e.g., networks, network bandwidth, servers, processing, memory, storage, applications, virtual machines (VMs), and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed and automatically, without requiring human interaction with the service's provider.

Broad network access: capabilities are available over a network and accessed through standard mechanisms that promote use by heterogeneous, thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned and, in some cases, automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active consumer accounts). Resource usage can be monitored, controlled, and reported, thereby providing transparency for both the provider and consumer of the utilized service.

Service Models are as follows:

Software as a Service (SaaS): the capability provided to the consumer is the ability to use the provider's applications running on a cloud infrastructure. The applications are accessible from various client devices through a thin client interface, such as a web browser (e.g., web-based email). The consumer does not manage or control the underlying cloud infrastructure including network, servers, operating systems, storage, or even individual application capabilities, with the possible exception of limited consumer-specific application configuration settings.

Platform as a Service (PaaS): the capability provided to the consumer is the ability to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application-hosting environment configurations.

Infrastructure as a Service (IaaS): the capability provided to the consumer is the ability to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is a service oriented with a focus on statelessness, low coupling, modularity, and semantic interoperability. At the heart of cloud computing is an infrastructure comprising a network of interconnected nodes.

Referring now to FIG. 1, an illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as private, community, public, or hybrid clouds as described hereinabove, or a combination thereof. This allows the cloud computing environment 50 to offer infrastructure, platforms, and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 2:
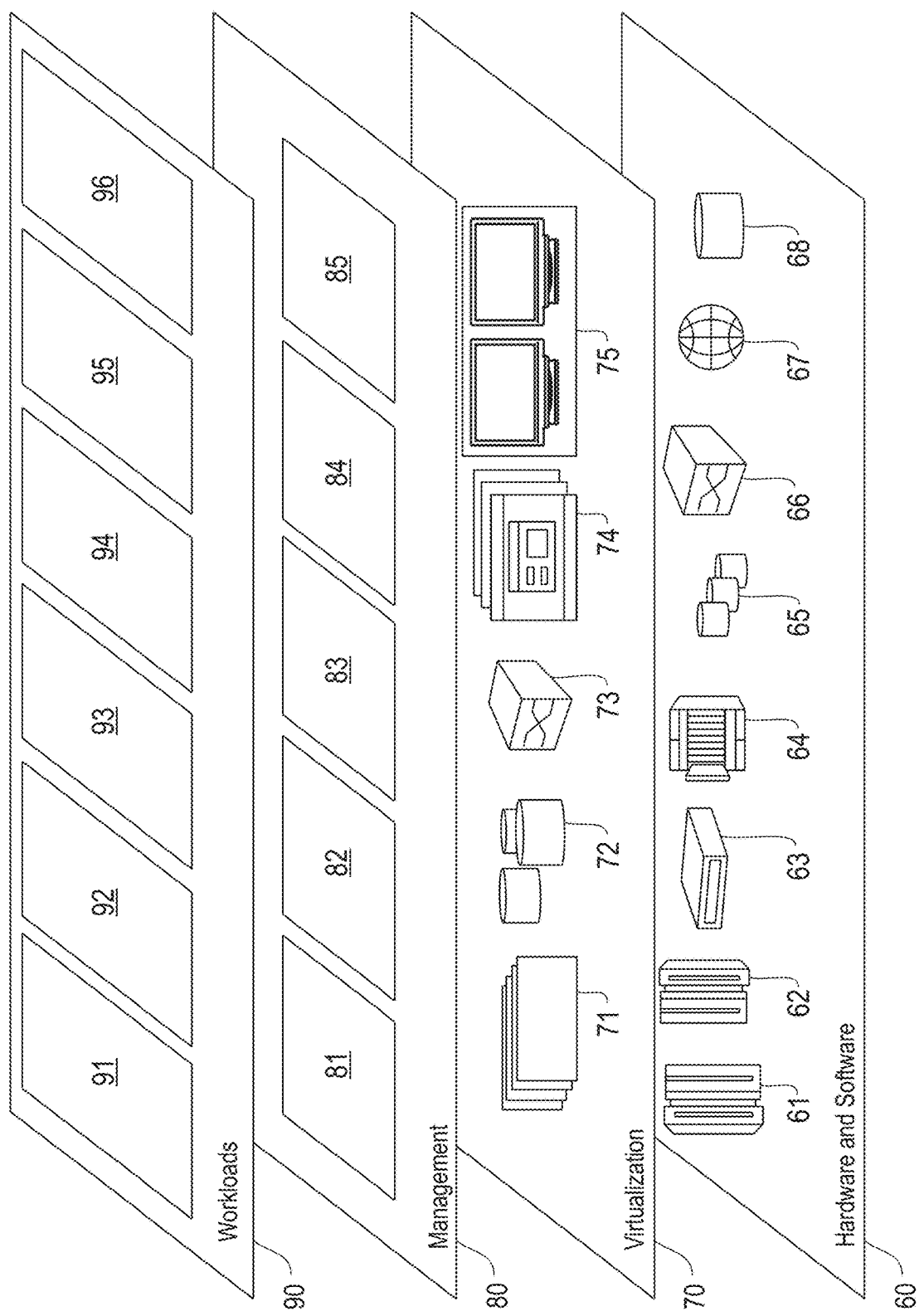
FIG. 2 depicts a set of abstraction model layers, according to an embodiment.

Referring now to FIG. 2, a set of functional abstraction layers provided by the cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, a management layer 80 may provide the functions described below. Resource provisioning 81 provides dynamic procurement of computing resources and other resources that are utilized to perform tasks within the cloud computing environment. Metering and pricing 82 provide cost tracking as resources are utilized within the cloud computing environment and billing or invoicing for consumption of these resources. In one example, these resources may comprise application software licenses. Security provides identity verification for cloud consumers and tasks as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and genomic distance, diagnostics testing, microbiological testing, clinical testing, and test design processing 96. As mentioned above, all of the foregoing examples described with respect to FIG. 2 are illustrative only, and the invention is not limited to these examples.

It is understood all functions of one or more embodiments as described herein may be typically performed by the processing system 300 (FIG. 3) or the cloud environment 410 (FIG. 4), which can be tangibly embodied as hardware processors and with modules of program code. However, this need not be the case for non-real-time processing. Rather, for non-real-time processing the functionality recited herein could be carried out/implemented and/or enabled by any of the layers 60, 70, 80 and 90 shown in FIG. 2.

It is reiterated that although this disclosure includes a detailed description on cloud computing, implementation of the teachings recited herein are not limited to a cloud computing environment. Rather, the embodiments of the present invention may be implemented with any type of clustered computing environment now known or later developed.

Whole genome distances may be rendered as a heat map. A matrix of 360,000×360,000 genomes, however, is too large to render on a display or in a simple static image—thus limiting its practical use for exploratory design or diagnostic applications. One embodiment provides a dynamic viewer tool that provides for user visualization in a dynamic, zoomable fashion, the genomic distance between a set of genomes, the genomic distance between target(s) and a large database of genomes for diagnostic test, microbiological test, clinical test, test design applications, etc.

Figure 3:
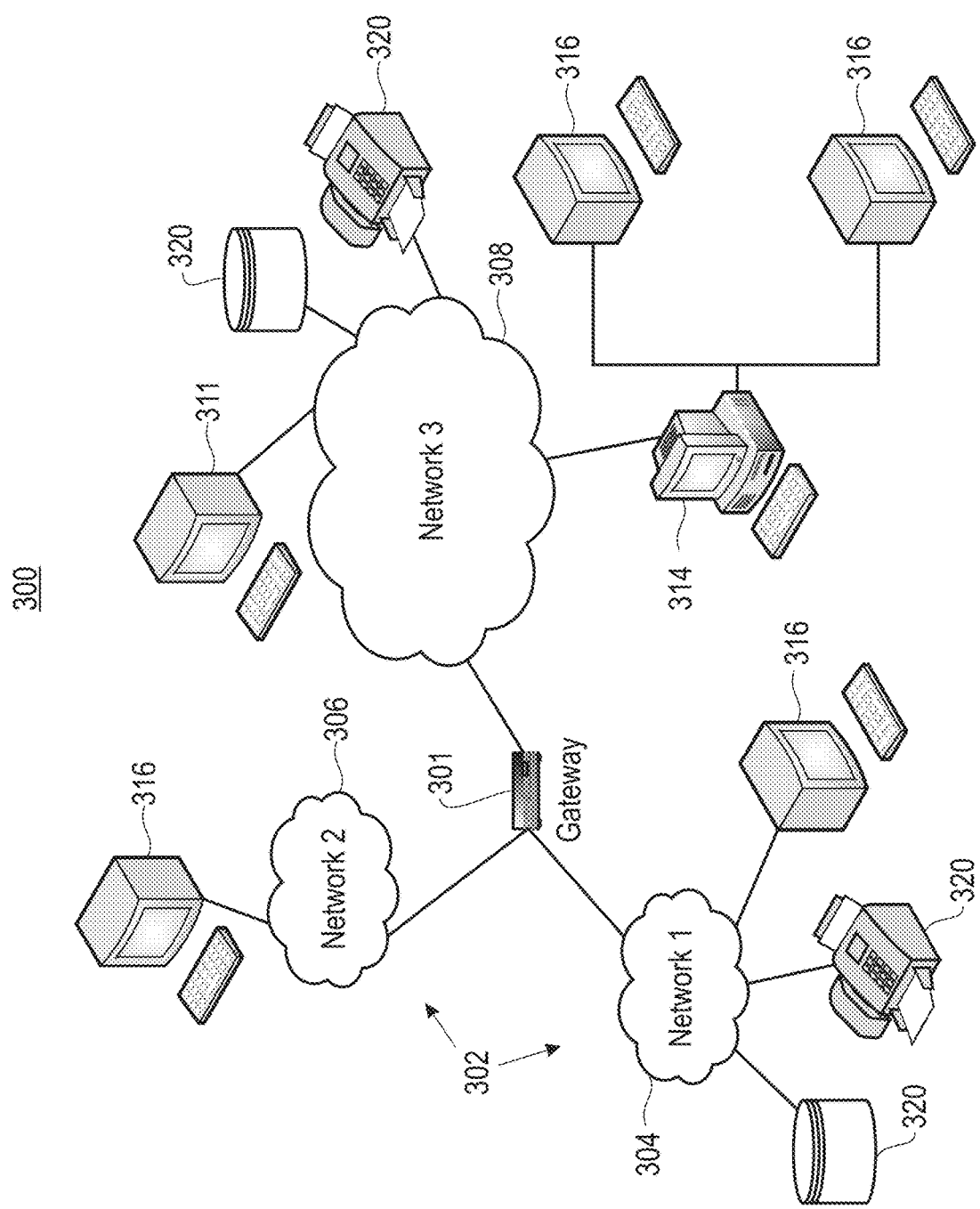
FIG. 3 is a network architecture for a multi-master distributed data management system, according to an embodiment.

FIG. 3 illustrates a network architecture 300, in accordance with one embodiment. As shown in FIG. 3, a plurality of remote networks 302 are provided, including a first remote network 304 and a second remote network 306. A gateway 301 may be coupled between the remote networks 302 and a proximate network 308. In the context of the present network architecture 300, the networks 304, 306 may each take any form including, but not limited to, a LAN, a WAN, such as the Internet, public switched telephone network (PSTN), internal telephone network, etc.

In use, the gateway 301 serves as an entrance point from the remote networks 302 to the proximate network 308. As such, the gateway 301 may function as a router, which is capable of directing a given packet of data that arrives at the gateway 301, and a switch, which furnishes the actual path in and out of the gateway 301 for a given packet.

Further included is at least one data server 314 coupled to the proximate network 308, which is accessible from the remote networks 302 via the gateway 301. It should be noted that the data server(s) 314 may include any type of computing device/groupware. Coupled to each data server 314 is a plurality of user devices 316. Such user devices 316 may include a desktop computer, laptop computer, handheld computer, printer, and/or any other type of logic-containing device. It should be noted that a user device 311 may also be directly coupled to any of the networks in some embodiments.

A peripheral 320 or series of peripherals 320, e.g., facsimile machines, printers, scanners, hard disk drives, networked and/or local storage units or systems, etc., may be coupled to one or more of the networks 304, 306, 308. It should be noted that databases and/or additional components may be utilized with, or integrated into, any type of network element coupled to the networks 304, 306, 308. In the context of the present description, a network element may refer to any component of a network.

According to some approaches, methods and systems described herein may be implemented with and/or on virtual systems and/or systems, which emulate one or more other systems, such as a UNIX system that emulates an IBM z/OS environment, a UNIX system that virtually hosts a MICROSOFT WINDOWS environment, a MICROSOFT WINDOWS system that emulates an IBM z/OS environment, etc. This virtualization and/or emulation may be implemented through the use of VMWARE software in some embodiments.

Figure 4:
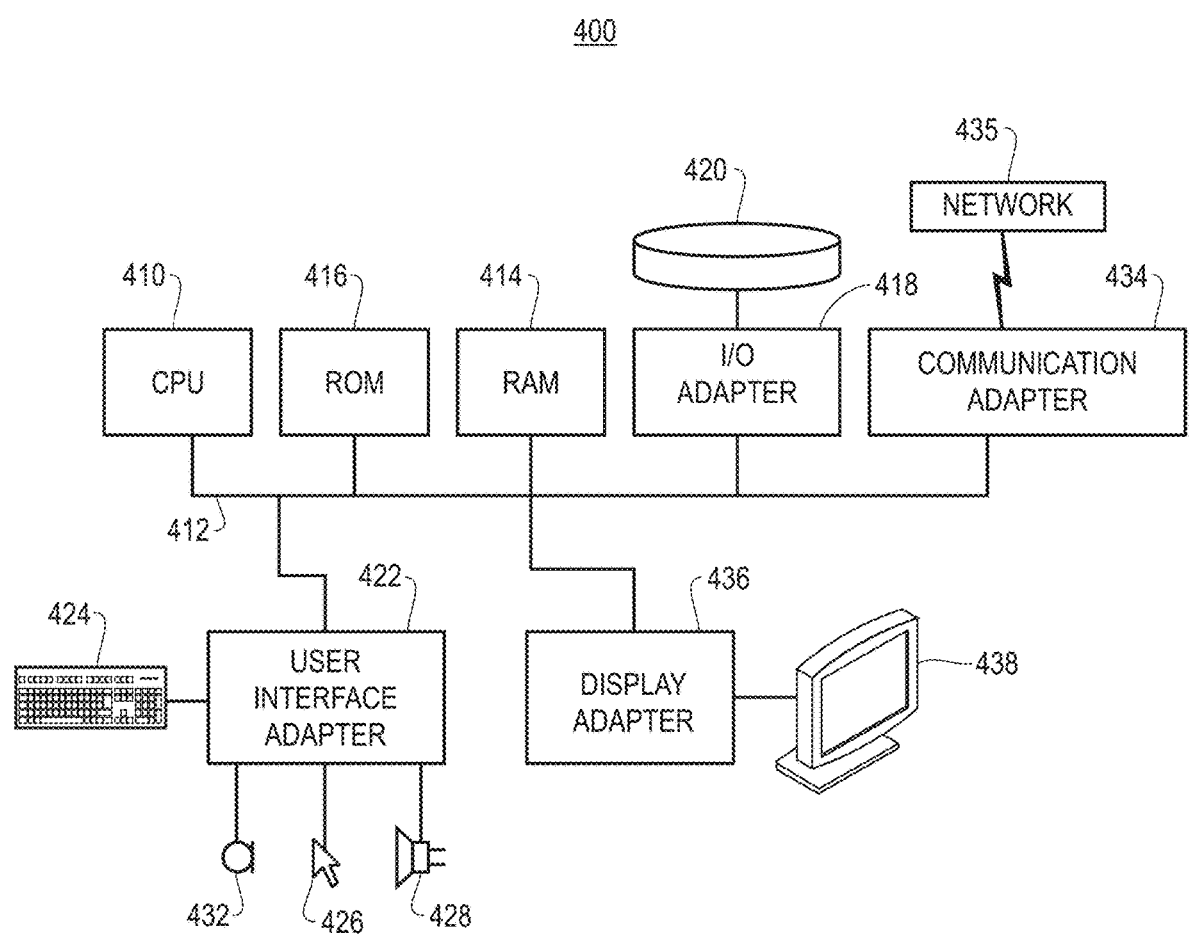
FIG. 4 shows a representative hardware environment that may be associated with the servers and/or clients of FIG. 1, according to an embodiment.

FIG. 4 shows a representative hardware system 400 environment associated with a user device 316 and/or server 314 of FIG. 3, in accordance with one embodiment. In one example, a hardware configuration includes a workstation having a central processing unit 410, such as a microprocessor, and a number of other units interconnected via a system bus 412. The workstation shown in FIG. 4 may include a Random Access Memory (RAM) 414, Read Only Memory (ROM) 416, an I/O adapter 418 for connecting peripheral devices, such as disk storage units 420 to the bus 412, a user interface adapter 422 for connecting a keyboard 424, a mouse 426, a speaker 428, a microphone 432, and/or other user interface devices, such as a touch screen, a digital camera (not shown), etc., to the bus 412, communication adapter 434 for connecting the workstation to a communication network 435 (e.g., a data processing network) and a display adapter 436 for connecting the bus 412 to a display device 438.

In one example, the workstation may have resident thereon an operating system, such as the MICROSOFT WINDOWS Operating System (OS), a MAC OS, a UNIX OS, etc. In one embodiment, the system 400 employs a POSIX® based file system. It will be appreciated that other examples may also be implemented on platforms and operating systems other than those mentioned. Such other examples may include operating systems written using JAVA, XML, C, and/or C++ language, or other programming languages, along with an object oriented programming methodology. Object oriented programming (OOP), which has become increasingly used to develop complex applications, may also be used.

Figure 5:
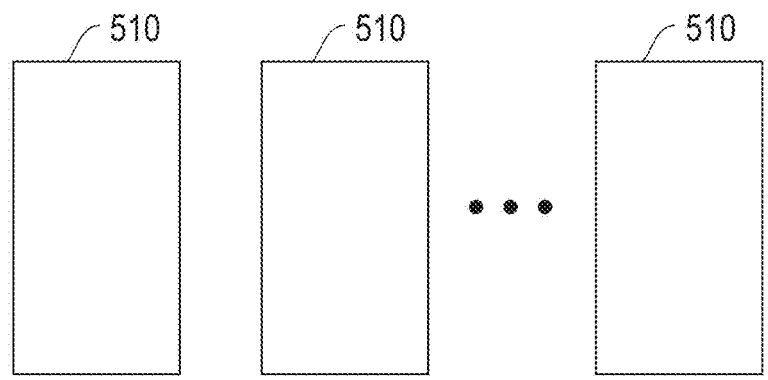
FIG. 5 is a block diagram illustrating a distributed system for selectively controlling visual content of biological sequence-sequence distances for a complete biological collection, according to one embodiment.
Figure 5:
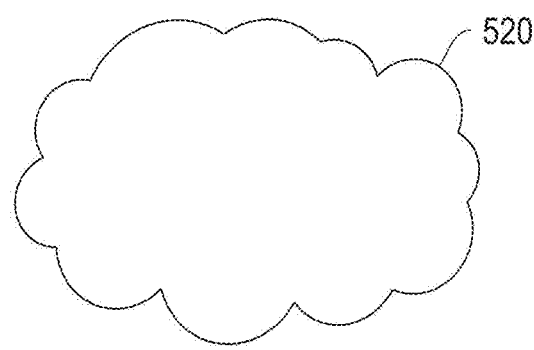
Figure 5:
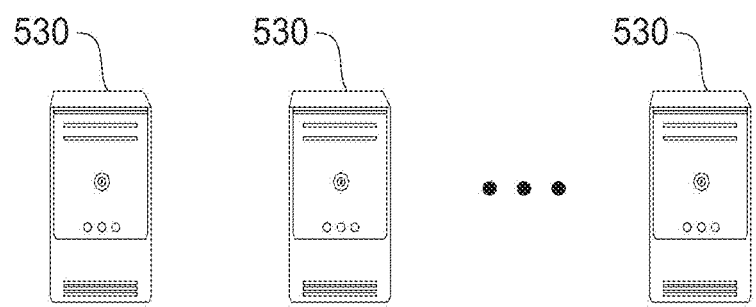

FIG. 5 is a block diagram illustrating a system 500 that may be employed for genomic distance, diagnostics testing, microbiological testing, clinical testing, and test design processing, according to one embodiment. In one embodiment, the system 500 includes client devices 510 (e.g., mobile devices, smart devices, computing systems, etc.), a cloud or resource sharing environment 520 (e.g., a public cloud computing environment, a private cloud computing environment, a datacenter, etc.), and servers 530. In one embodiment, the client devices are provided with cloud services from the servers 530 through the cloud or resource sharing environment 520.

In the system 500, the client devices 510 may use one or more embodiments for the following applications. The client devices 510 may be used for heredity applications including: disease factors, genes, prenatal screening, paternity testing, etc. The client devices 510 may be applied for classification of animal breeds (e.g., for pets, livestock, etc.); disease: prognosis (e.g., for cancer, etc.), diagnosis (e.g., cancer, etc.). The client devices 510 may be used for organism detection: pathogen detection: viruses (quasispecies characterization); bacteria: distribution of genetic composition, distribution of quasispecies, etc. Further applications may include detection of genetically modified organisms (GMO), for engineered organisms (Biosecurity), detecting hybrids, for food safety applications, and for gene function (antibiotic, livestock traits, plant traits, etc.).

Some embodiments may use the client devices 510 for a dynamic zoomable visualization distance explorer for determining/representing heredity of an organism or set of organisms: for classification of: domesticated animals (e.g., dog breeds, cat breeds, steers, etc.); for a dynamic zoomable visualization distance explorer determining/representing prognosis of an individual based on genetic similarity to a set related cases (e.g., cancer, etc.); a dynamic zoomable visualization distance explorer determining/representing diagnosis of an individual based on genetic similarity to a set related cases; a dynamic zoomable visualization distance explorer to determining/representing the distribution of organisms with similarity to a nucleic acid sequence or set of sequences: in order to: detect and characterize a quasispecies of viruses; detect and characterize a population of bacteria; detect and characterize a population of Fungi; determine/represent genes that produce a defined phenotype of an organism and/or community of organisms: that change the yield of a chemical or compound or complex product; that allows for the production of a chemical or compound not typical of the organism; determine/regulate the sex of the organism; determine/regulate the sterility of the organism; that change the tolerance of the organism to an environmental condition: temperature (high or low); moisture; salinity; low concentration of chemical or compound in the environment; and high concentration of chemical or compound in the environment; to determine/represent genetic modification of an organism for food safety: detection of genetically modified plants (that change the yield of a chemical or compound or complex product; that allows for the production of a chemical or compound not typical of the organism; determine/regulate the sex of the organism; determine/regulate the sterility of the organism; that change the tolerance of the organism to an environmental condition: temperature (high or low), moisture, salinity, low concentration of chemical or compound in the environment, and high concentration of chemical or compound in the environment; detect of genetically modified animals: that change the yield of a chemical or compound or complex product; that allows for the production of a chemical or compound not typical of the organism; determine/regulate the sex of the organism; determine/regulate the sterility of the organism; that change the tolerance of the organism to an environmental condition: temperature (high or low), moisture, salinity, low concentration of chemical or compound in the environment, and high concentration of chemical or compound in the environment; to determine/represent genetic modification of an organism for biosecurity: detection of insertion of sequences that change the phenotype of an organism: detection of insertion of virulence genes, detection of insertion of antibiotic resistance genes, detection of insertion of sequences that change the niche of an organism, and detection of insertion of sequences that change the mode of transmission of an organism; for antibiotic resistance; virulence genes; livestock traits; and plant traits: changing the yield of a product and change the tolerance of an organism to extreme environments.

Some embodiments may use the client devices 510 for configuration of a pop-up bubble for dynamic zoomable visualization distance explorer that displays metadata of the organism(s) represented. Another application of the client devices 510 may be for a dynamic zoomable visualization distance explorer representing the members of a set that are detected by a biological or chemical detection technique: detection by: nucleic acid based amplification techniques (e.g., polymerase chain reaction (PCR)); protein based amplification techniques; nucleic acid based hybridization techniques; protein based hybridization techniques; serological techniques; chemical based amplification techniques and chemical based hybridization techniques. Other applications of the client devices 510 may include a dynamic zoomable visualization distance explorer predicting the members of a set that are detected by a biological or chemical detection technique for detection by: nucleic acid based amplification techniques; protein based amplification techniques; nucleic acid based hybridization techniques; protein based hybridization techniques; serological techniques; chemical based amplification techniques; and chemical based hybridization techniques.

Figure 6:
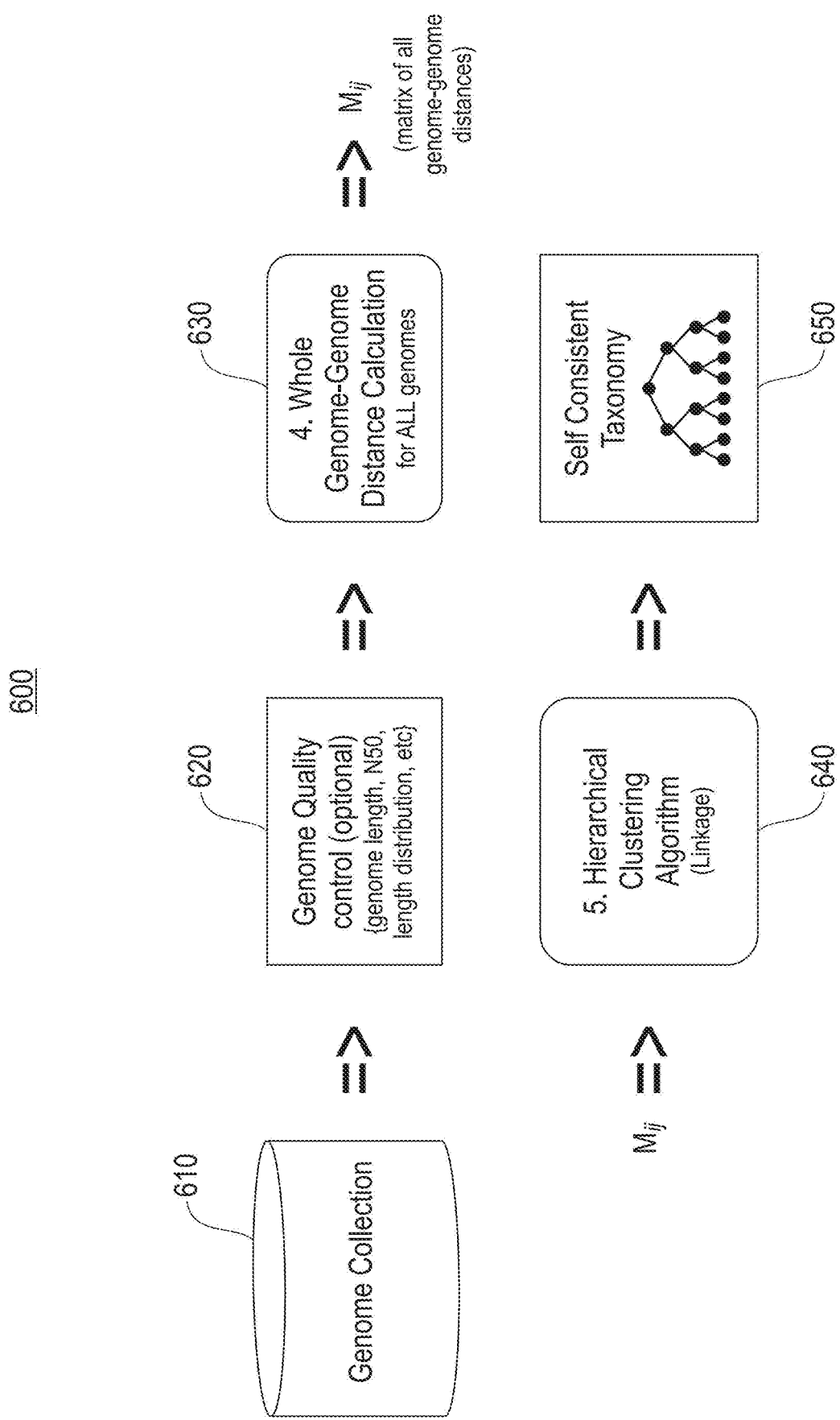
FIG. 6 illustrates a block diagram for a process to construct a self-consistent taxonomy, according to one embodiment.
Figure 7:
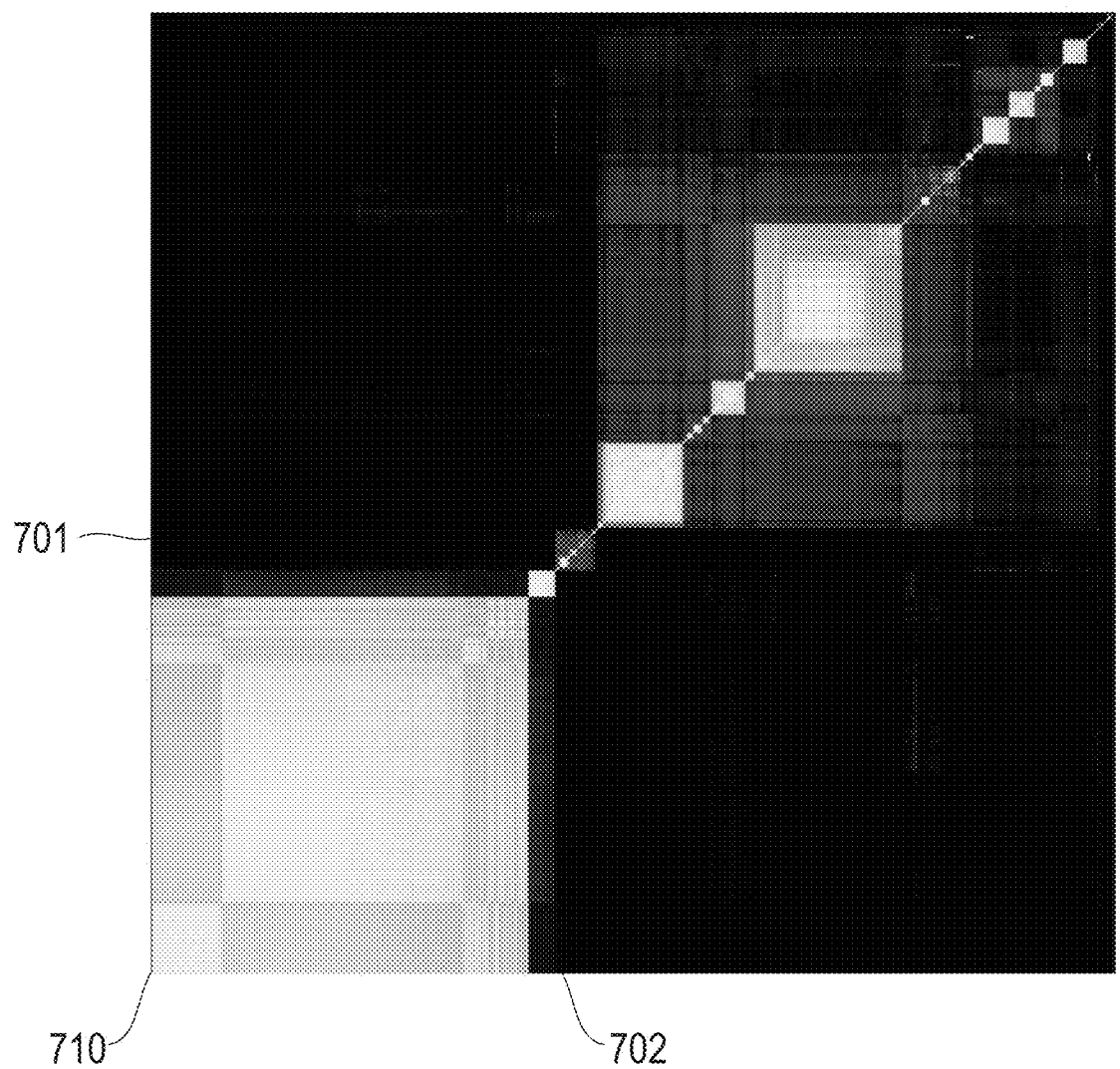
FIG. 7 illustrates an example static heat map image of size 1250×1250 showing whole genome-genome distance between all *Salmonella* genomes in the public RefSeq library, according to one embodiment.

FIG. 6 illustrates a block diagram for a process 600 to construct a self-consistent taxonomy, according to one embodiment. In the process 600, one intermediate result is the generation of a matrix $M_{ij}$ of all genome-genome, gene-gene, protein-protein, or (in general) sequence-sequence distances, where i and j are positive integers (and represent row and column, respectively). The process 600 may be implemented using a number of algorithms, such as MinHash or the Meier-Kolthoff methodologies. In one embodiment, a sequence (genome) collection 610 (or other sequence collection, such as genes, proteins, nucleic acid, biological domains, etc.) are obtained as input to the process 600. In one embodiment, genome (or other sequence) quality control may be applied to the sequence collection 610. This optional quality control 620 may include, for example, genome length, length of distribution, etc. Next the process 600 performs whole sequence-sequence (e.g., genome-genome, gene-gene, protein-protein, etc.) distance calculations 630 for the complete sequence collection 610, forming the matrix $M_{ij}$. The matrix $M_{ij}$ is then used as input to a hierarchical clustering algorithm 640, such as linkage that computes the self-consistent taxonomy 650 from the actual difference (or similarity) between the respective sequences (e.g., genomes, genes, etc.). The order of the Leaf nodes in the self-consistent hierarchical clustering produced by linkage can be used to sort the elements i,j (rows and columns) of the matrix $M_{ij}$. This sorted matrix may then be rendered as a heat map 700 (FIG. 7). In one embodiment, the matrix $M_{ij}$ may be generated or processed by distributing the computations over a collection of processing devices, such as multi-processors, servers (e.g., cloud servers, physical servers, etc.), etc. Each processing device receives a portion of the matrix $M_{ij}$ computation to perform (e.g., in parallel). The final result of the $M_{ij}$ is assembled together from the processing devices. In one embodiment, the self-consistent hierarchical clustering produced by linkage (minimum spanning tree) is performed by the collection of processing devices (e.g., in parallel).

FIG. 7 illustrates an example 700 of static heat map image 702 of size~1250×1250 showing whole genome-genome distance between all *Salmonella* genomes in the public RefSeq library, according to one embodiment. The heat map image 700 includes the X axis 701, Y axis 702 and the diagonal line 710 where X=Y. This static image of size~1250×1250 shows the whole genome-genome distance between all *Salmonella* genomes in the public RefSeq library. The bright yellow squares along the diagonal line 710 are different subspecies or serovars of *Salmonella*. There are over 60,000 public *Salmonella* genomes available today. Fine structure (detailed distance variation) is evident between genomes of the same serotype, but it is impossible to render a matrix with resolution 60,000×60,000 in an image of size 1250×1250. To address this problem, in one embodiment a dynamic sequence (e.g., genome) explorer 800 (FIG. 8) provides the ability to zoom-in and zoom-out of the full resolution matrix where each increase of magnification provides a higher resolution view of the data.

Figure 8:
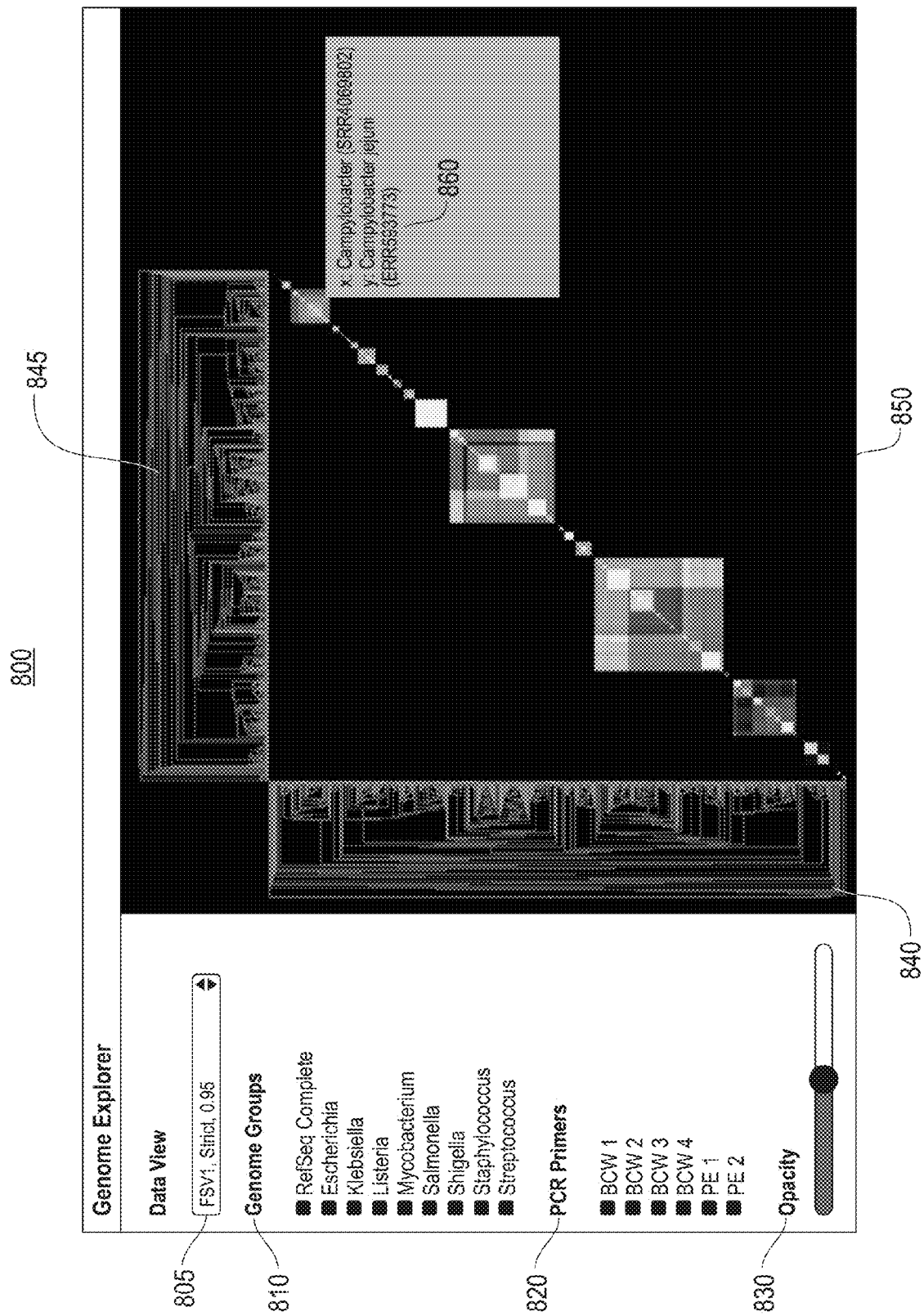
FIG. 8 illustrates an example sequence explorer running as a web application (in a browser), according to one embodiment.

FIG. 8 illustrates an example sequence explorer 800 running as a web application (in a browser), according to one embodiment. In the example genome-genome panel 850, over 170,000 high quality genomes from 60 different genera are rendered in the sequence explorer 800. Each heat map panel in FIGS. 8-11 (i.e., heat map panel 850, heat map panel 950, heat map panel 1050 and heat map panel 1150, respectively) shows the same data at increasing magnification up to a resolution showing the genomic distance between individual genomes. The zoom function may be activated by, for example, a mouse, up/down arrows on the keyboard, a finger expansion/pinch on a touch screen, a sensed hand gesture, voice command, etc. At the location of a pointer on the heat map panel 850, an optional metadata window 860 appears showing information about the two genomes $G_i$ and $G_j$, at location x,y in the displayed image. In one embodiment, the sequence explorer 800 may include metadata selections. For example, the sequence explorer 800 may include data view 805 (e.g., selected data from a drop-down menu), genome groups 810, PCR primers 820, etc. On the left-side and the upper-side of the heat map panel 850, taxonomic tree segments 840 and 845 show the hierarchical clustering (e.g., linkage, etc.) used to sort the heat map 850. This is shown in white as a taxonomic tree. The taxonomic tree also dynamically scan and zooms with the heat map 850 image.

In one embodiment, the metadata selections information displayed may be configurable by a properties definition. The metadata information may include, for example, the accession number of each genome, the whole genome-genome distance value (also visible as the color of the selected coordinate in the heat map panel 850 of $M_{ij}$), the taxonomic name with taxonomic rank, etc.

Figure 9:
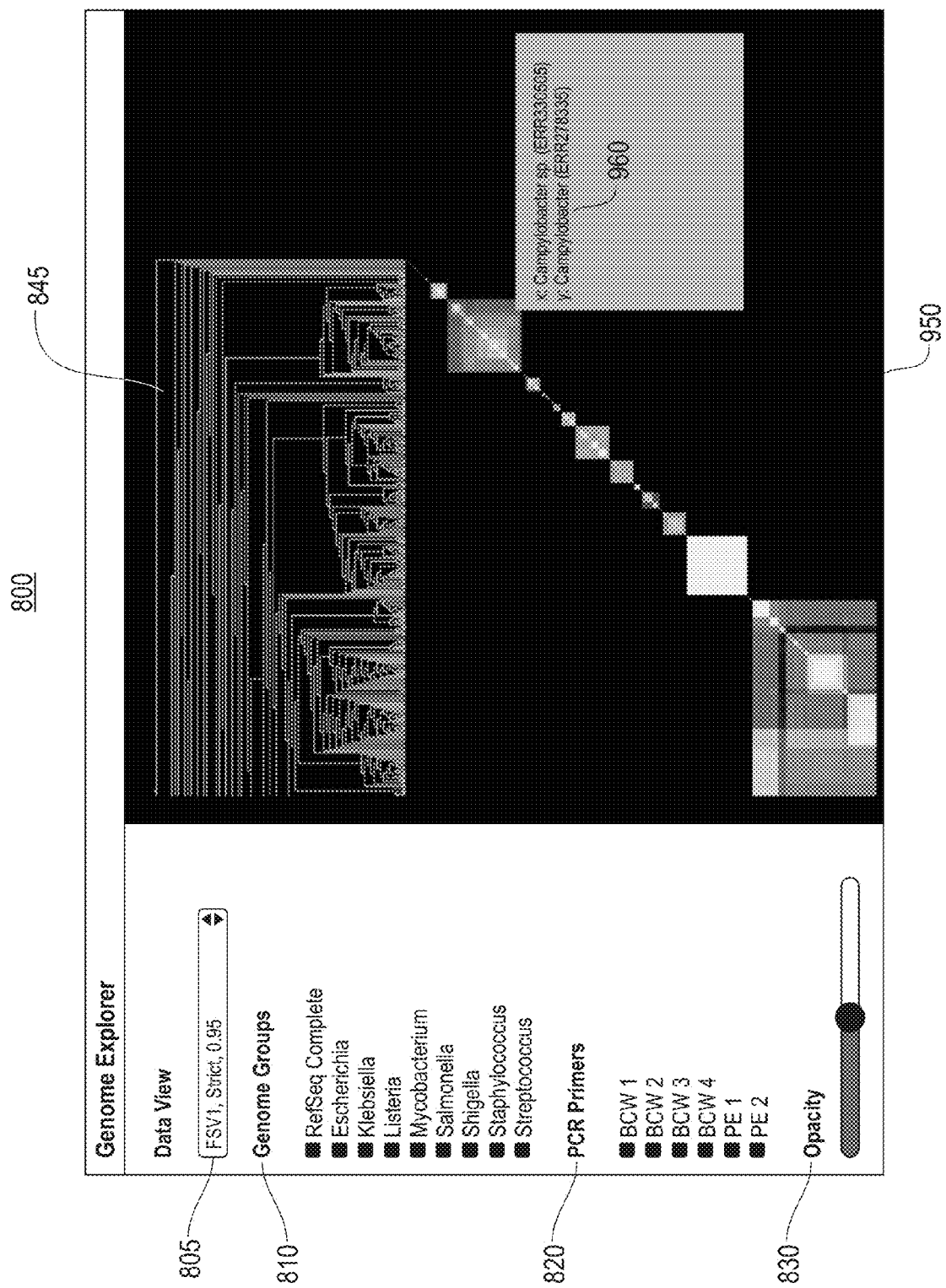
FIG. 9 illustrates the example sequence explorer of FIG. 8 shown at a first increased magnification, according to one embodiment.

FIG. 9 illustrates the example sequence explorer 800 of FIG. 8 shown at a first increased magnification, according to one embodiment. The zoomed-in heat map panel 950 is shown magnified from the heat map panel 850 (FIG. 8). At the location of a pointer on the heat map panel 950, an optional metadata window 960 appears showing information about the two genomes $G_i$ and $G_j$, at location x,y in the displayed image. On the upper-side of the heat map panel 950, a taxonomic tree segment 845 is also zoomed-in since the taxonomic tree dynamically scans and zooms with the heat map panel 950 image.

Figure 10:
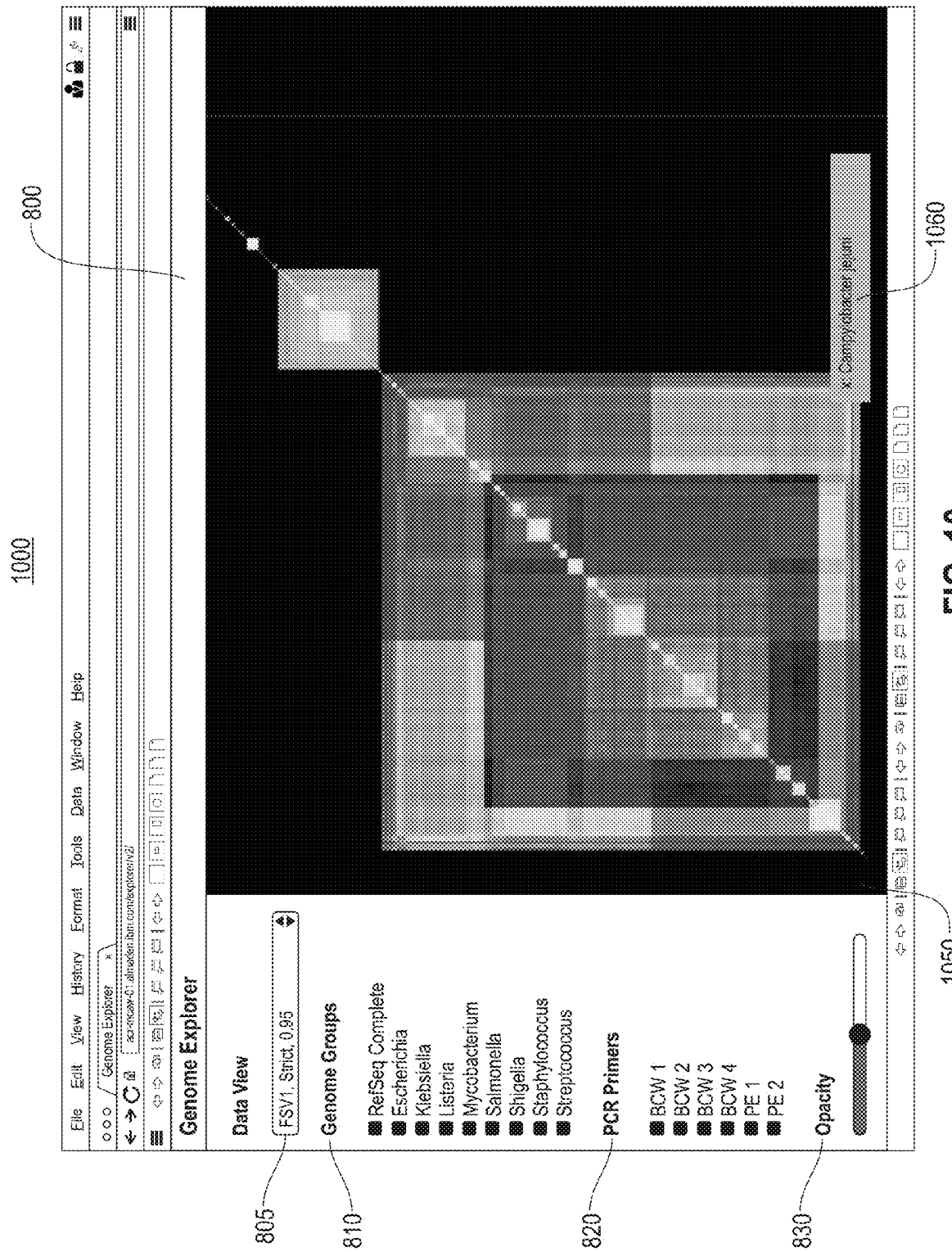
FIG. 10 illustrates the example sequence explorer of FIG. 8 shown at a second increased magnification, according to one embodiment.

FIG. 10 illustrates the example sequence explorer 800 of FIG. 8 shown at a second increased magnification, according to one embodiment. The sequence explorer in this example is shown in browser 1000. The zoomed-in heat map panel 1050 is shown magnified from the heat map panel 950 (FIG. 9). At the location of a pointer on the heat map panel 1050, an optional metadata window 1060 appears showing information about the two genomes $G_i$ and at location x,y in the displayed image. Note that based on the magnification from zooming-in, the taxonomic tree is not shown due to the magnification of the heat map panel 950.

Figure 11:
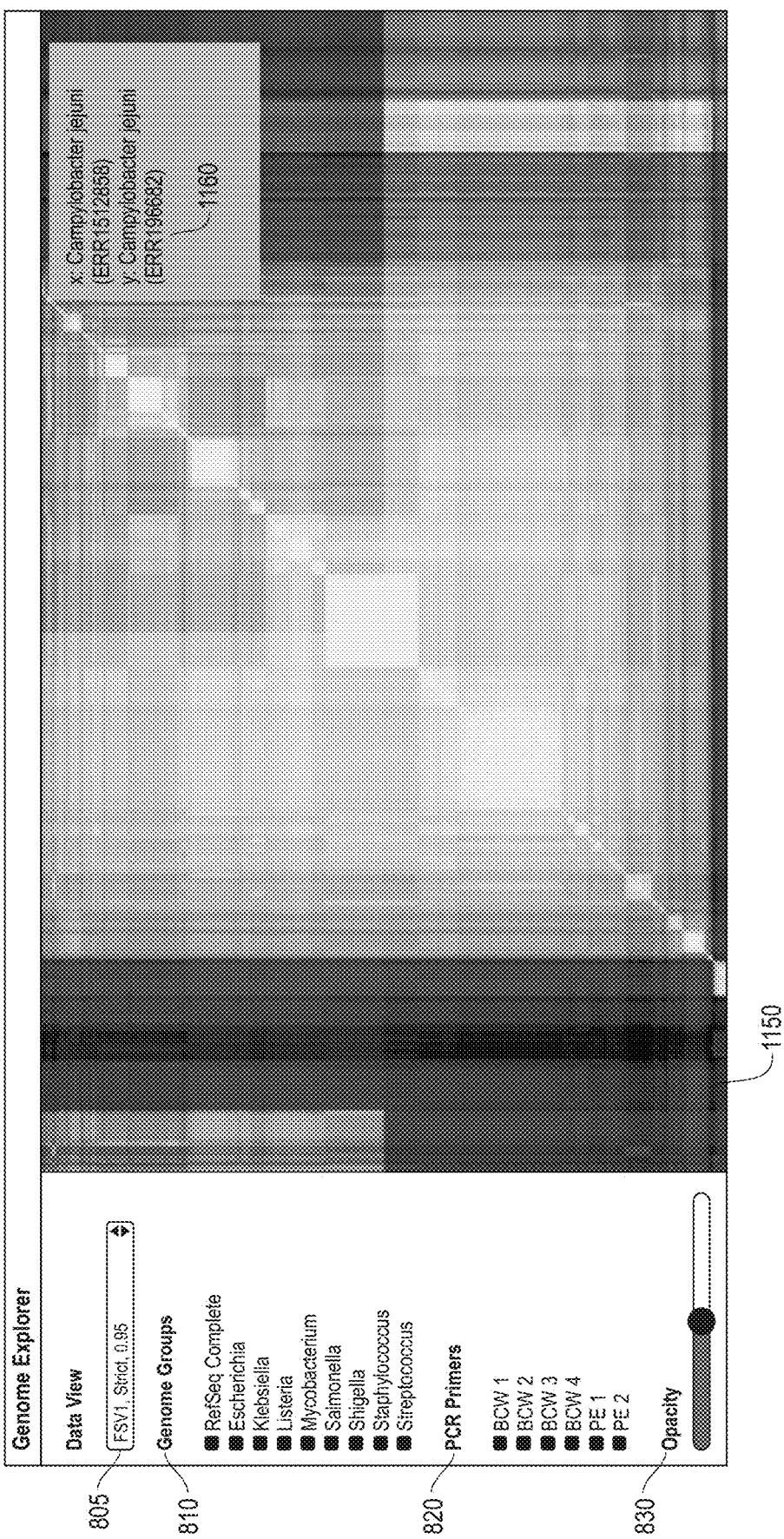
FIG. 11 illustrates the example sequence explorer of FIG. 8 shown at a third increased magnification, according to one embodiment.

FIG. 11 illustrates the example sequence explorer 800 of FIG. 8 shown at a third increased magnification, according to one embodiment. The zoomed-in heat map panel 1150 is shown magnified from the heat map panel 1050 (FIG. 10). At the location of a pointer on the heat map panel 1150, an optional metadata window 1160 appears showing information about the two genomes $G_i$ and $G_j$, at location x,y in the displayed image. Note that based on the magnification from zooming-in, the taxonomic tree is not shown due to the magnification of the heat map panel 1150.

Figure 12:
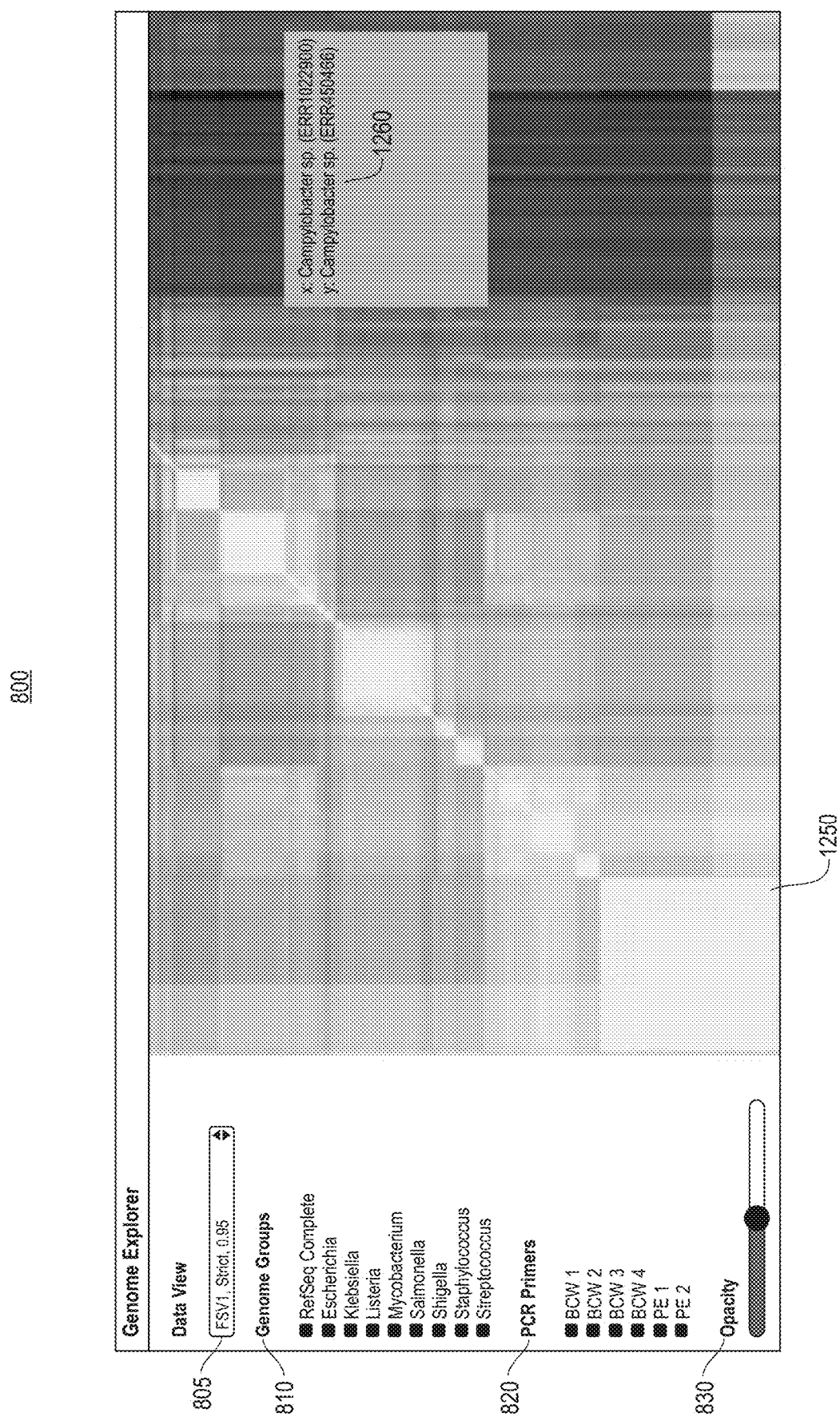
FIG. 12 illustrates the example sequence explorer of FIG. 8 shown at a fourth increased magnification, according to one embodiment.

FIG. 12 illustrates the example sequence explorer 800 of FIG. 8 shown at a fourth increased magnification, according to one embodiment. The zoomed-in heat map panel 1250 is shown magnified from the heat map panel 1150 (FIG. 11). At the location of a pointer on the heat map panel 1250, an optional metadata window 1260 appears showing information about the two genomes $G_i$ and $G_j$, at location x,y in the displayed image. Note that based on the magnification from zooming-in, the taxonomic tree is not shown due to the magnification of the heat map panel 1250.

Figure 13:
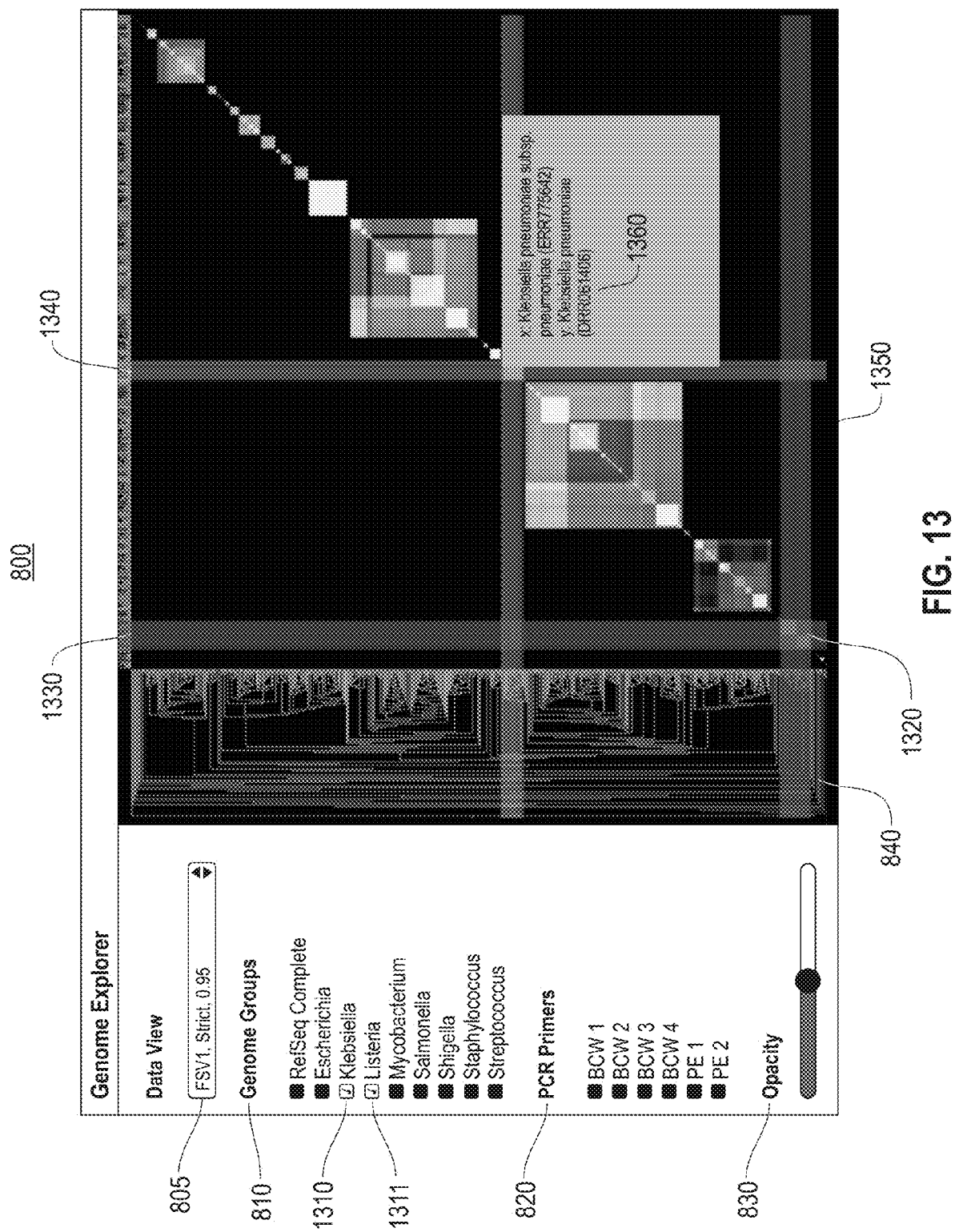
FIG. 13 illustrates an example of the sequence explorer implemented in a diagnostic or clinical application, according to one embodiment.

FIG. 13 illustrates an example of the sequence explorer 800 implemented in a diagnostic or clinical application, according to one embodiment. In this application of the sequence explorer 800 showing the heat map panel 1350, a translucent overlay (see slider labeled "opacity" 830) of configurable color is used to highlight all example of genomes within a selected group. The group may be a particular serovar or species already within the reference database, or it may be a group defined by sequence data from a set of biological or medical samples. For example in a large foodborne disease outbreak samples taken from many patients (or many food samples, factories, or factory tools) will often be obtained. Measuring whole genome-genome distance (sequence collection 610, FIG. 6) between these samples with each other and/or with the reference database is then used to highlight the 'nearest' reference genomes to the samples. Here nearest is defined as those reference genomes with the smallest whole genome-genome distance to each sample. In this example, different groups are shown at once (in the example both *Klebsiella* 1310 and *Listeria*

1311). In a diagnostic application, clinicians are more likely to view one set at a time. For this example, the translucent overlay 1330 is selected for *Listeria* 1311 and the translucent overlay 1340 is selected for *Klebsiella* 1310. At the location of a pointer on the heat map panel 1350, an optional metadata window 1360 appears showing information about the two genomes $G_i$ and $G_j$, at location x,y in the displayed image. On the left-side of the heat map panel 1350, a taxonomic tree segment 840 is shown. The intersection 1320 of the translucent overlay 1330 shows where x=y.

Figure 14:
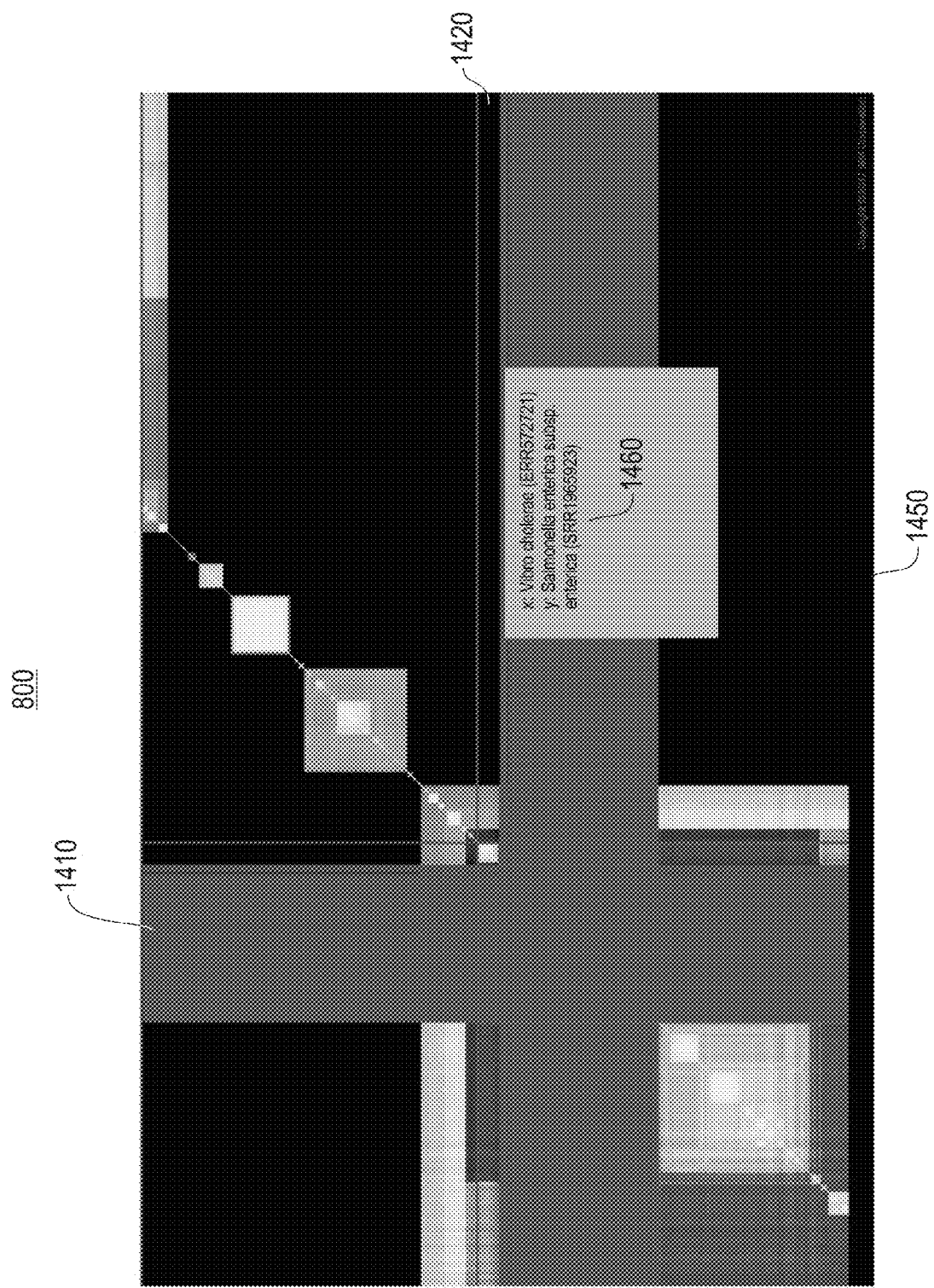
FIG. 14 illustrates an example of the sequence explorer implemented to verify polymerase chain reaction (PCR) primer design, according to one embodiment.

FIG. 14 illustrates an example of the sequence explorer 800 implemented to verify PCR primer design, according to one embodiment. Many microbiological testing and rapid testing applications make use of "primers." A "primer" is a short RNA or DNA sequence that serves as a starting point for DNA synthesis. A primer is required because the enzymes that catalyze DNA synthesis can only add nucleotides to an existing strand (i.e., they require a starting point or primer). With a suitable primer, a target sequence of DNA may be used to amplify only those DNA molecules within a sample that have the target sequence. If the target sequence is, for example, unique to a particular pathogenic organism, the PCR primer (combined with a simple color change reaction) may be used to rapidly determine if the DNA sample contains (comes from) the organisms in question. This is rapid PCR. It is used for many clinical and biosafety applications. The test requires that:
1. The PCR primer molecule is built from a sequence in a particular target organism. This determines the test's ability to be sensitive to true positive samples.
2. The PCR primer is specific to the target and not to DNA from organisms not in the target group. This determines the ability of the test to be specific (low or zero false positives). Selecting a sequence with high specificity and high sensitivity is the process of PCR primer design. To be approved by the Food and Drug Administration (FDA), a primers' specificity and sensitivity must be verified.

In one embodiment, the heat map panel 1450 shows how the sequence explorer 800 is used for PCR primer design and verification. A provided sequence is entered and all genomes that contain the sequence (or that contain sequences within a specified distance from the target are highlighted with a color overlay 1410). The sequence is designed to hit a particular taxonomic group visible as square regions in the sequence explorer 800. Genomes within the target serotype that should be "hit" by the target sequence but are not, are evident as black lines in the vertical and horizontal bands overlaying the target serotype in the highlighted color overlay 1410. These black lines indicate likely false negative test results. Conversely, the color overlay 1410 that hits genomes outside of the target group (e.g., indicated by line 1420) identify likely false positive (FP) test results. The true positive (TP) rate (TPR), and false positive rates (FPR) can be measured directly with the sequence explorer 800 and reported as:

$$TRP = \frac{\sum TP}{\sum \text{condition positive}}$$

and $$FPR = \frac{\sum FP}{\sum \text{condition negative}}$$

At the location of a pointer on the heat map panel 1450, an optional metadata window 1460 appears showing information about the two genomes $G_i$ and $G_j$, at location x,y in the displayed image.

Figure 15:
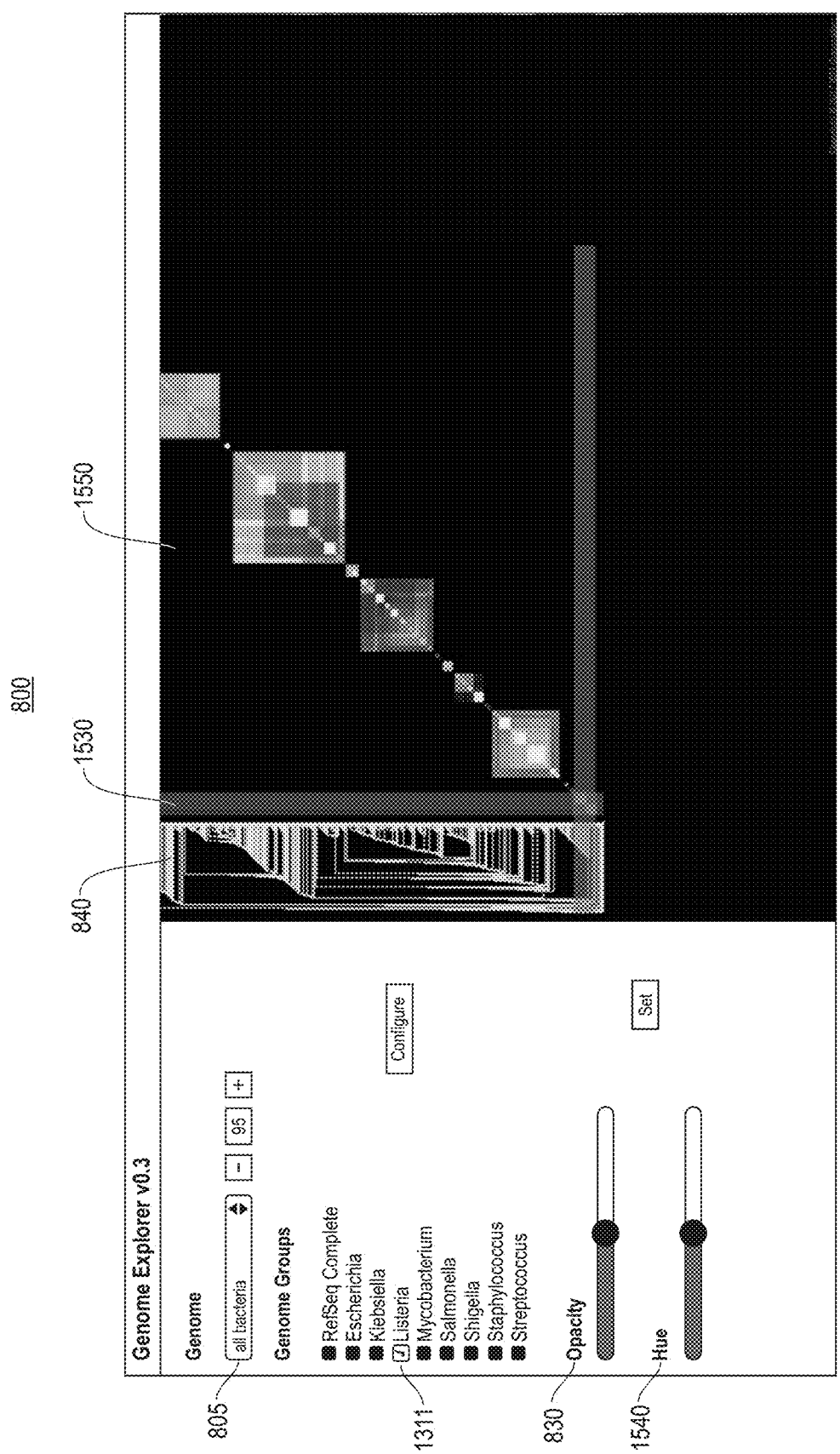
FIG. 15 illustrates an example of the sequence explorer with a selectable hue configuration, according to one embodiment.

FIG. 15 illustrates an example of the sequence explorer 800 with a selectable hue configuration 1540, according to one embodiment. In one embodiment, the selectable opacity configuration 830 is also available. The translucent overlay 1530 of configurable color is used to highlight all example of genomes within a selected group. On the left-side of the heat map panel 1550, a taxonomic tree segment 840 is shown. In this example, *Listeria* 1311 is selected. In this example, a default opacity configuration 830 and a default hue configuration 1540 are shown, and the translucent overlay 1530 is selected for *Listeria* 1311.

Figure 16:
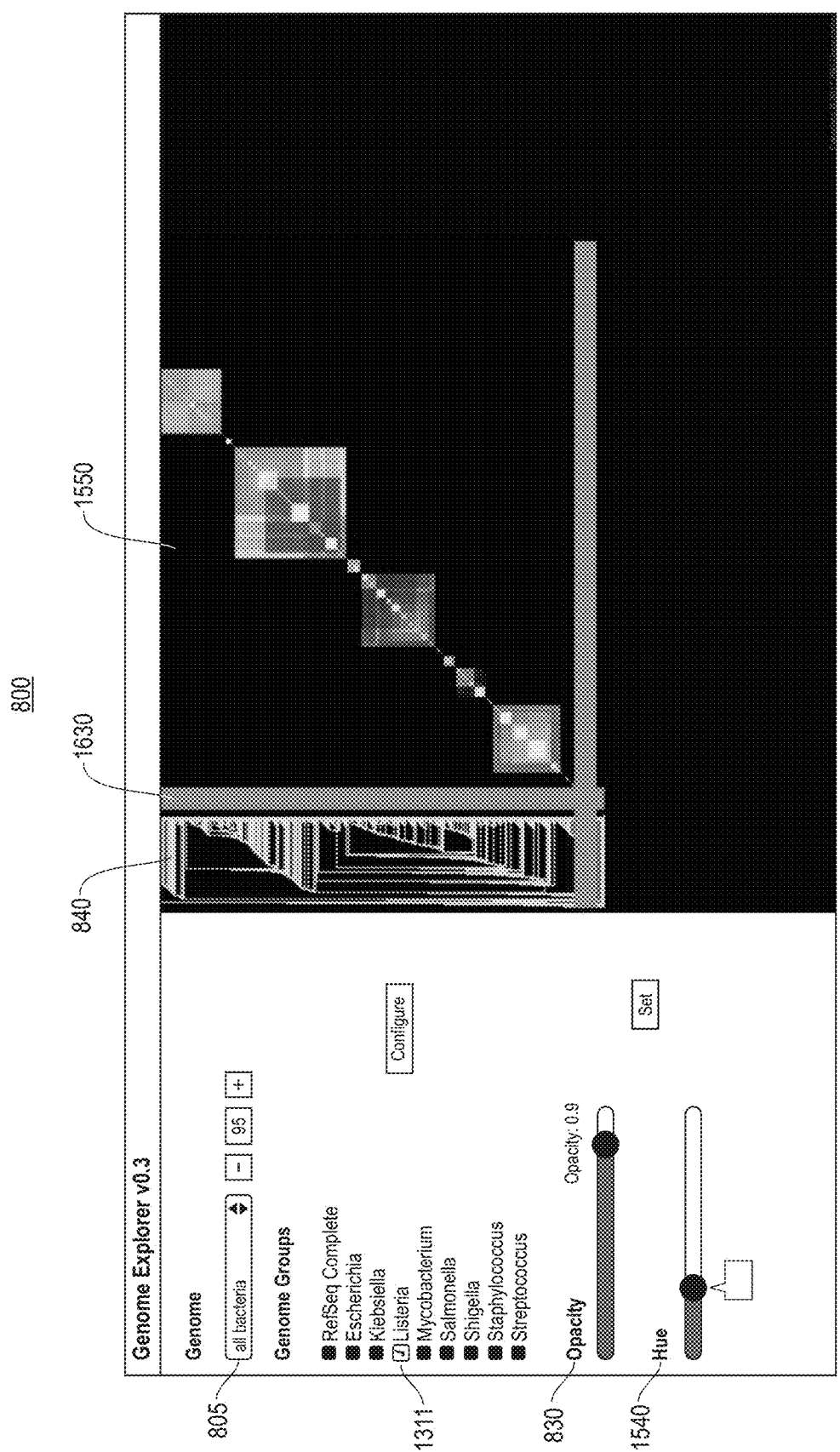
FIG. 16 illustrates the example of the sequence explorer of FIG. 15 with a particular opacity and hue set, according to one embodiment.

FIG. 16 illustrates the example of the sequence explorer 800 of FIG. 15 with a particular opacity 830 and hue 1540 set, according to one embodiment. In this example, the opacity 830 is set to 0.9 (out of 1.0) and the hue 1540 is selected as a shade of green. In this example, *Listeria* 1311 is selected and the translucent overlay 1630 is selected for the *Listeria* 1311.

Figure 17:
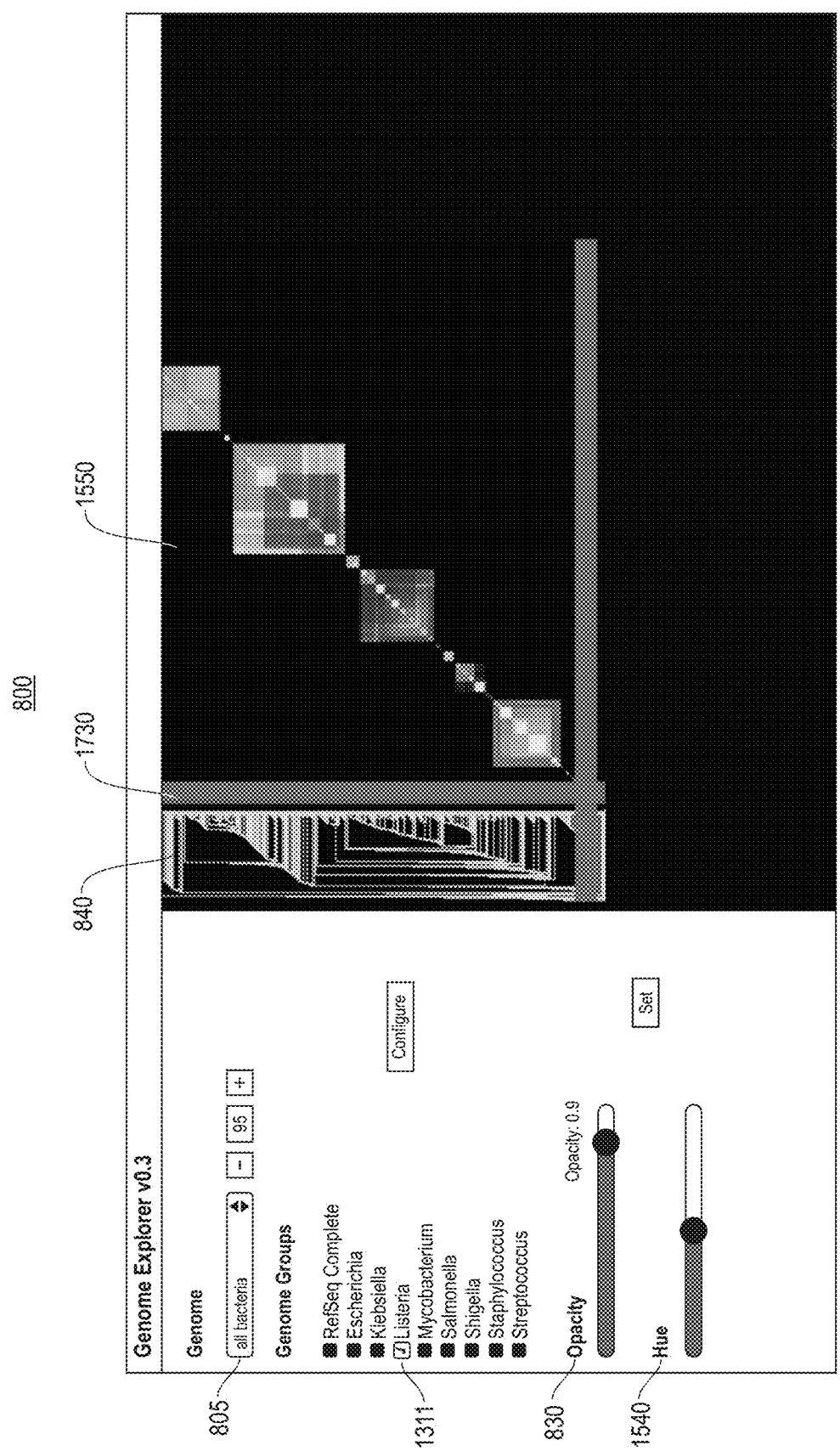
FIG. 17 illustrates the example of the sequence explorer of FIG. 15 with another opacity and hue set, according to one embodiment.

FIG. 17 illustrates the example of the sequence explorer 800 of FIG. 15 with another opacity 830 and hue 1540 set, according to one embodiment. In this example, the opacity 830 is set to 0.9 (out of 1.0) and the hue 1540 is selected as a shade of pink. In this example, *Listeria* 1311 is selected and the translucent overlay 1730 is selected for the *Listeria* 1311.

FIG. 18 illustrates an example graphical user interface (GUI) 1800 for inputting a sequence, according to one embodiment. In one embodiment, the GUI 1800 may be part of an initial set-up or dynamic initialization for the sequence explorer 800, as described above. In one embodiment, the GUI 1800 includes an input for name or identification (ID) 1810, group 1820, sequence 1830 and a selection 1840 for uploading the sequence inputs. In some embodiments, the sequence inputs may be free-hand entered, selected from a drop-down list, selected from a pop-up window list, searched for, etc.

Figure 19:
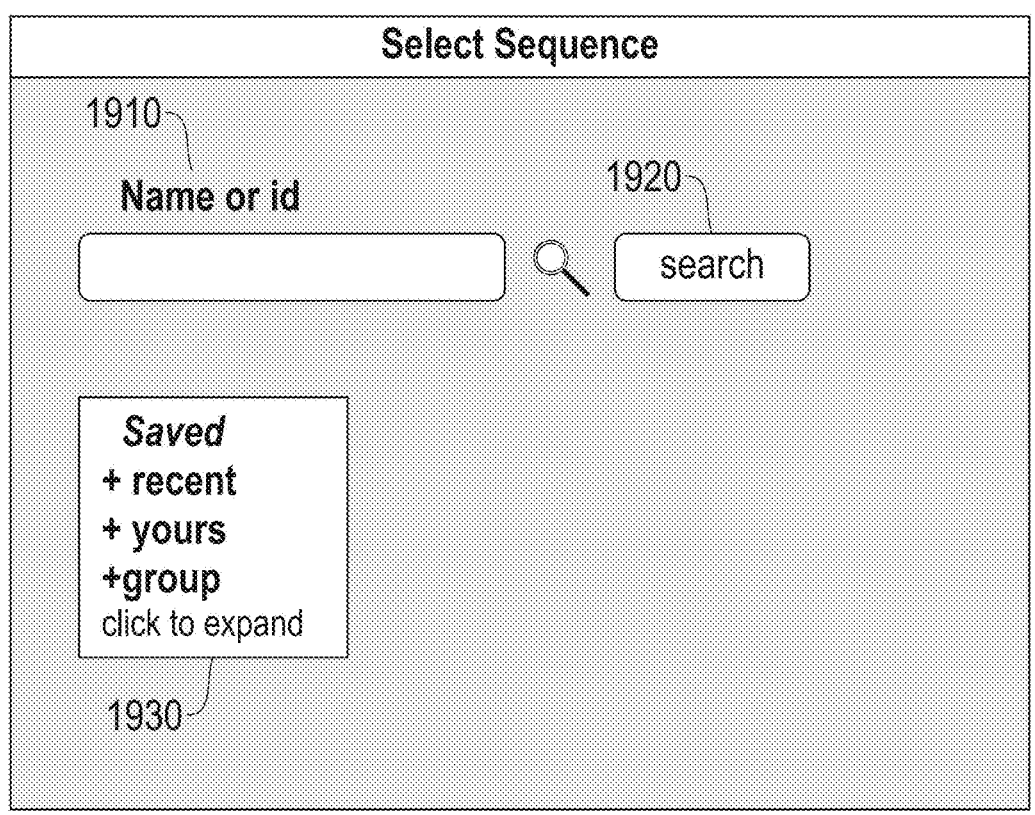
FIG. 19 illustrates an example GUI for selecting a sequence, according to one embodiment.

FIG. 19 illustrates an example GUI 1900 for selecting a sequence, according to one embodiment. In one embodiment, the GUI 1900 may be part of an initial set-up or dynamic initialization for the sequence explorer 800, as described above. In one embodiment, the GUI 1900 includes an input for name or ID 1910, search 1920 and a selection 1930 for selecting saved recent, yours (a user's saved input), and group saved input, which the lists may be expanded. In some embodiments, the sequence inputs may be free-hand entered, selected from a drop-down list, selected from a pop-p window list, searched for, etc.

Figure 20:
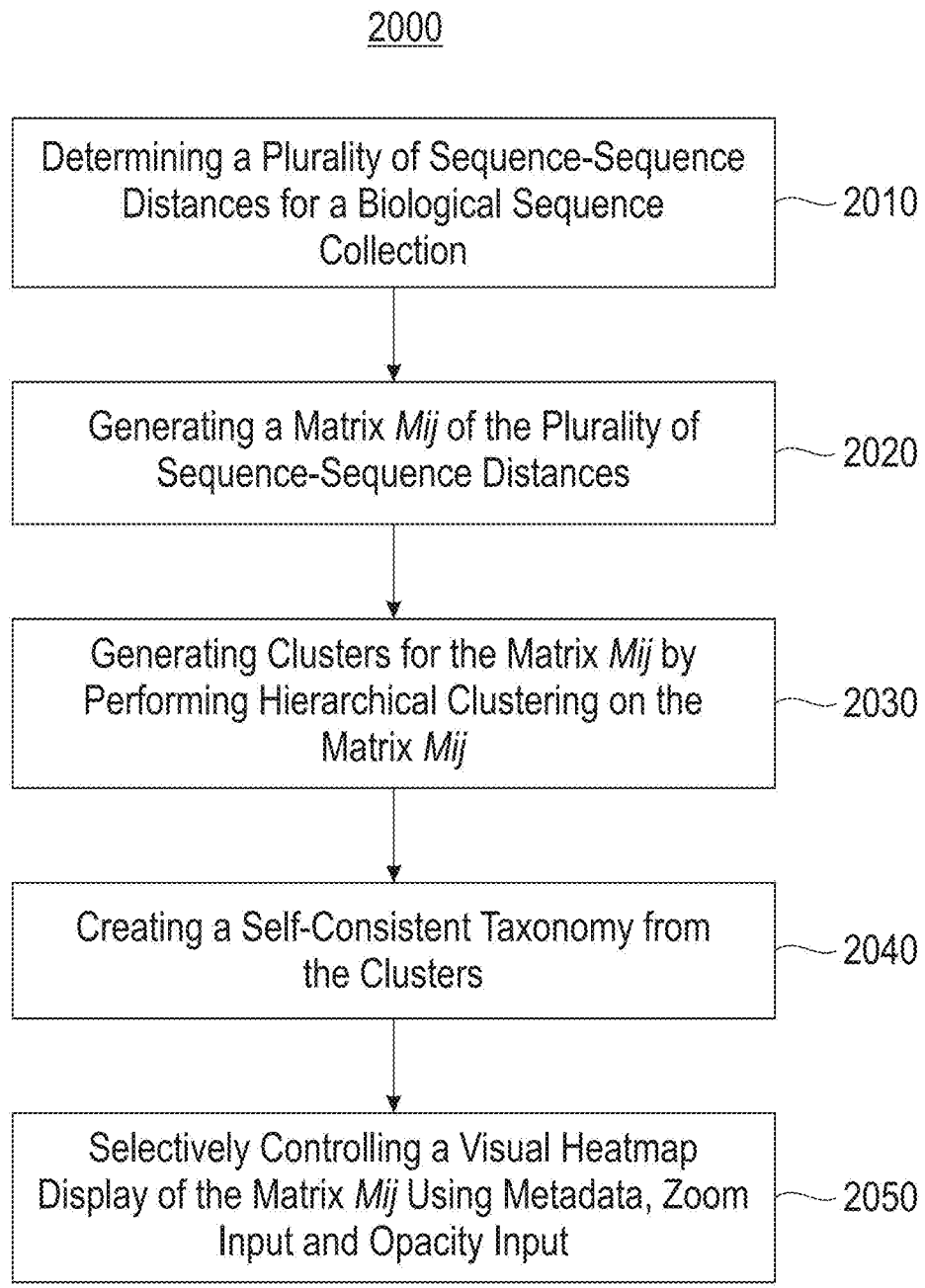
FIG. 20 illustrates a block diagram for a process for selectively controlling visual content of biological sequence-sequence distances for a complete biological collection, according to one embodiment.

FIG. 20 illustrates a block diagram for process 2000 for selectively controlling visual content of biological sequence-sequence distances for a complete biological collection, according to one embodiment. In one embodiment, in block 2010 process 2000 includes determining, by at least one processor (e.g., a multi-processor, a set of processors, at least one processor or at least one computing device from computing environment 50 (FIG. 1), network architecture 300 (FIG. 3), hardware system 400 (FIG. 4), or system 500 (FIG. 5)), multiple sequence-sequence distances for a biological sequence collection (e.g., sequence (genome) collection 610, FIG. 6). In block 2020, process 2000 generates, by the at least one processor, a matrix $M_{ij}$ of the multiple sequence-sequence distances (i and j are positive integers and represent rows and columns, respectively). In block 2030, process 2000 generates, by the at least one processor, clusters for the matrix $M_{ij}$ by performing hierarchical clustering (e.g., hierarchical clustering 640, FIG. 6) on the matrix In block 2040, process 2000 creates a self-consistent taxonomy (e.g., self-consistent taxonomy 650, FIG. 6) from the clusters. In block 2050, process 2000 selectively controls a visual heat map (e.g., heat map 850, FIG. 8) display of the matrix $M_{ij}$ using metadata, zoom input and opacity input.

In one embodiment, for process 2000 the sequence collection may include at least one of: genomes, genes, proteins, nucleic acid, and biological domains. In some embodiments, the metadata includes: at least one group of: genomes, PCR primers, genes, proteins, nucleic acid and biological domains. The zoom input may include zoom-in input and zoom-out input. Selectively controlling the visual heat map display of the matrix $M_{ij}$ may further include using selectable hue input.

In one embodiment, for process 2000 the hierarchical clustering may be based on at least one of: MinHash clustering, Meier-Kolthoff clustering, clustered from sequence distances by sequence alignment, agglomerative clustering, and divisive hierarchical clustering. In one embodiment, the agglomerative and divisive hierarchical clustering are ordered using one of: a single linkage clustering process, a complete linkage clustering process, an average linkage clustering process, and a centroid linkage clustering process.

In one embodiment, the visual heat map display represents members of a set based on detecting one of a biological and a chemical detection process. In one embodiment, the detecting may include detection by: nucleic acid based amplification, protein based amplification, nucleic acid based hybridization, protein based hybridization, a serological process, chemical based amplification, and chemical based hybridization.

In one embodiment, process 2000 may further include generating a bubble display that is overlaid on the heat map, where the bubble display may include a configurable metadata that includes at least one of: genome accession, genome taxonomy identification (TaxID), gene features, functional features and most effective medicinal treatment.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
   generating, by an at least one processor, a matrix based on a plurality of sequence-sequence distances for a biological sequence collection;
   generating, by the at least one processor, clusters by performing hierarchical clustering on the matrix;
   creating a taxonomic tree based on the clusters;
   sorting elements of the matrix based on an order of leaf nodes of the taxonomic tree;
   rendering the matrix with the sorted elements as a visual heat map;
   displaying a visualization comprising the visual heat map and the taxonomic tree, wherein the taxonomic tree dynamically scans and zooms with the visual heat map; and verifying polymerase chain reaction (PCR) primer design of a PCR primer by:
      receiving, as input, a provided sequence that the PCR primer is built on, wherein the provided sequence is designed to hit a target sequence of DNA from a target group of organisms;
      generating a first overlay highlighting one or more portions of the visual heat map, wherein the one or more portions highlighted by the first overlay include all genomes that contain the provided sequence;
      identifying false negative test results by generating a second overlay highlighting one or more portions of the first overlay, wherein the second overlay includes genomes within the target sequence of DNA from the target group that are not included in the provided sequence;
      identifying false positive test results by generating a third overlay highlighting one or more other portions of the first overlay, wherein the third overlay include genomes outside of the target sequence of DNA from the target group, and wherein the first overlay, the second overlay, and the third overlay have different colors;
      measuring false positive rates based on the false positive test results identified; and
      determining specificity of the PCR primer based on the false positive rates.

2. The method of claim 1, wherein the sequence collection comprises at least one of: a sequence of genomes, a sequence of genes, a sequence of proteins, and a sequence of nucleic acids.

3. The method of claim 1, further comprising:
   controlling the visualization displayed using metadata, zoom input, and opacity input, wherein the controlling comprises:
      providing a higher resolution view of the matrix by increasing magnification of a portion of the visual heat map and a taxonomic tree segment of the taxonomic tree in response to the zoom input including zoom-in input; and
      generating a fourth overlay highlighting the portion of the visual heat map and the taxonomic tree segment by adjusting opacity of the portion of the visual heat map and the taxonomic tree segment in response the opacity input;
   wherein the metadata comprises information about at least one group of: genomes, PCR primers, genes, proteins, nucleic acids, and biological domains;
   wherein the zoom input comprises the zoom-in input and a zoom-out input from an input/output device; and
   wherein the controlling further comprises adjusting hue of the fourth overlay in response to a selectable hue input.

4. The method of claim 1, wherein the hierarchical clustering is based on at least one of: MinHash clustering, Meier-Kolthoff clustering, clustering from sequence distances by sequence alignment, agglomerative clustering, and divisive hierarchical clustering.

5. The method of claim 4, wherein the agglomerative clustering and the divisive hierarchical clustering includes one of:
   a single linkage clustering process;
   a complete linkage clustering process;
   an average linkage clustering process; and
   a centroid linkage clustering process.

6. The method of claim 1, wherein the visual heat map represents members of a set based on one of a biological detection process and a chemical detection process.

7. The method of claim 6, wherein the biological detection process and the chemical detection process includes at least one of:
   nucleic acid based amplification; and
   nucleic acid based hybridization.

8. The method of claim 1, further comprising:
   generating a bubble display that is overlaid on the visual heat map, wherein the bubble display comprises metadata indicative of at least one of: a genome accession, a genome taxonomy identification (TaxID), and gene features.

9. A non-transitory computer program product comprising a computer readable storage medium having program instructions embodied therewith, the program instructions configured so as to be executable by at least one processor to cause the at least one processor to:
   determine, by the at least one processor, a plurality of sequence-sequence distances for a biological sequence collection;
   generate, by the at least one processor, a matrix based on the plurality of sequence-sequence distances;
   generate, by the at least one processor, clusters by performing hierarchical clustering on the matrix;
   create, by the at least one processor, a taxonomic tree based on the clusters;
   sort elements of the matrix based on an order of leaf nodes of the taxonomic tree;
   render the matrix with the sorted elements as a visual heat map;
   display, by the at least one processor, a visualization comprising the visual heat map and the taxonomic tree, wherein the taxonomic tree dynamically scans and zooms with the visual heat map; and
   verify, by the at least one processor, polymerase chain reaction (PCR) primer design of a PCR primer by:
      receiving, as input, a provided sequence that the PCR primer is built on, wherein the provided sequence is designed to hit a target sequence of DNA from a target group of organisms;
      generating a first overlay highlighting one or more portions of the visual heat map, wherein the one or more portions highlighted by the first overlay include all genomes that contain the provided sequence;
      identifying false negative test results by generating a second overlay highlighting one or more portions of the first overlay, wherein the second overlay include genomes within the target sequence of DNA from the target group that are not included in the provided sequence;
      identifying false positive test results by generating a third overlay highlighting one or more other portions of the first overlay, wherein the third overlay include genomes outside of the target sequence of DNA from the target group, and wherein the first overlay, the second overlay, and the third overlay have different colors;
      measuring false positive rates based on the false positive test results identified; and
      determining specificity of the PCR primer based on the false positive rates.

10. The computer program product of claim 9, wherein the sequence collection comprises at least one of: a sequence of genomes, a sequence of genes, a sequence of proteins, and a sequence of nucleic acids.

11. The computer program product of claim 9, wherein the program instructions are further executable by the at least one processor to cause the at least one processor to:
   control, by the at least one processor, the visualization displayed using metadata, zoom input, and opacity input, wherein the control comprises:
      providing a higher resolution view of the matrix by increasing magnification of a portion of the visual heat map and a taxonomic tree segment of the taxonomic tree in response to the zoom input including zoom-in input; and
      generating a fourth overlay highlighting the portion of the visual heat map and the taxonomic tree segment by adjusting opacity of the portion of the visual heat map and the taxonomic tree segment in response the opacity input;
   wherein the metadata comprises information about at least one group of: genomes, PCR primers, genes, proteins, nucleic acids, and biological domains;
   wherein the zoom input comprises the zoom-in input and a zoom-out input from an input/output device; and
   wherein the control further comprises adjusting hue of the fourth overlay in response to a selectable hue input.

12. The computer program product of claim 9, wherein the hierarchical clustering is based on at least one of: MinHash clustering, Meier-Kolthoff clustering, clustering from sequence distances by sequence alignment, agglomerative clustering, and divisive hierarchical clustering.

13. The computer program product of claim 12, wherein the agglomerative clustering and the divisive hierarchical clustering includes one of:
   a single linkage clustering process;
   a complete linkage clustering process;
   an average linkage clustering process; and
   a centroid linkage clustering process.

14. The computer program product of claim 9, wherein the visual heat map represents members of a set based on one of a biological detection process and a chemical detection process.

15. The computer program product of claim 14, wherein the biological detection process and the chemical detection process includes at least one of:
   nucleic acid based amplification; and
   nucleic acid based hybridization.

16. The computer program product of claim 9, wherein the program instructions are further executable by the at least one processor to cause the at least one processor to:
   generate, by the at least one processor, a bubble display that is overlaid on the visual heat map, wherein the bubble display comprises metadata indicative of at least one of: a genome accession, a genome taxonomy identification (TaxID), and gene features.

17. A system comprising:
   a memory storing instructions; and
   at least one processor that executes the instructions to perform a process comprising:

determining a plurality of sequence-sequence distances for a biological sequence collection;
generating a matrix based on the plurality of sequence-sequence distances;
generating clusters by performing hierarchical clustering on the matrix;
creating a taxonomic tree based on the clusters;
sorting elements of the matrix based on an order of leaf nodes of the taxonomic tree;
rendering the matrix with the sorted elements as a visual heat map;
displaying a visualization comprising the visual heat map and the taxonomic tree, wherein the taxonomic tree dynamically scans and zooms with the visual heat map; and
verifying polymerase chain reaction (PCR) primer design of a PCR primer by:
  receiving, as input, a provided sequence that the PCR primer is built on, wherein the provided sequence is designed to hit a target sequence of DNA from a target group of organisms;
  generating a first overlay highlighting one or more portions of the visual heat map, wherein the one or more portions highlighted by the first overlay include all genomes that contain the provided sequence;
  identifying false negative test results by generating a second overlay highlighting one or more portions of the first overlay, wherein the second overlay include genomes within the target sequence of DNA from the target group that are not included in the provided sequence;
  identifying false positive test results by generating a third overlay highlighting one or more other portions of the first overlay, wherein the third overlay include genomes outside of the target sequence of DNA from the target group, and wherein the first overlay, the second overlay, and the third overlay have different colors;
  measuring false positive rates based on the false positive test results identified; and
  determining specificity of the PCR primer based on the false positive rates.

18. The system of claim 17, wherein the process further comprises:
controlling the visualization displayed using metadata, zoom input, and opacity input, wherein the controlling comprises:

providing a higher resolution view of the matrix by increasing magnification of a portion of the visual heat map and a taxonomic tree segment of the taxonomic tree in response to the zoom input including zoom-in input; and
generating a fourth overlay highlighting the portion of the visual heat map and the taxonomic tree segment by adjusting opacity of the portion of the visual heat map and the taxonomic tree segment in response the opacity input;
wherein the metadata comprises information about at least one group of: genomes, PCR primers, genes, proteins, nucleic acids, and biological domains;
wherein the zoom input comprises the zoom-in input and a zoom-out input from an input/output device;
wherein the controlling further comprises adjusting hue of the fourth overlay in response to a selectable hue input; and
wherein the hierarchical clustering is based on at least one of: MinHash clustering, Meier-Kolthoff clustering, clustering from sequence distances by sequence alignment, agglomerative clustering, and divisive hierarchical clustering.

19. The system of claim 18, wherein:
the agglomerative clustering and the divisive hierarchical clustering includes one of:
  a single linkage clustering process;
  a complete linkage clustering process;
  an average linkage clustering process;
  a centroid linkage clustering process;
  the visual heat map represents members of a set based on one of a biological detection process and a chemical detection process; and
  the biological detection process and the chemical detection process includes at least one of:
    nucleic acid based amplification;
    and nucleic acid based hybridization.

20. The system of claim 17, wherein the process further comprises:
generating a bubble display that is overlaid on the visual heat map, wherein the bubble display comprises metadata indicative of at least one of: a genome accession, a genome taxonomy identification (TaxID), and gene features.

* * * * *